United States Patent [19]
Carmichael et al.

[11] Patent Number: 6,090,585
[45] Date of Patent: Jul. 18, 2000

[54] HUMAN COLLAGENASE INHIBITOR SEQUENCE, RECOMBINANT VECTOR SYSTEM FOR USING SAME AND RECOMBINANT-DNA METHOD FOR THE MANUFACTURE OF SAME

[75] Inventors: David F. Carmichael; David C. Anderson, both of Louisville, Colo.; George P. Stricklin, Germantown, Tenn.; Howard G. Welgus, St. Louis, Mo.

[73] Assignee: Amgen Inc., Thousand Oaks, Calif.

[21] Appl. No.: 08/474,553

[22] Filed: Jun. 7, 1995

Related U.S. Application Data

[63] Continuation of application No. 08/050,739, Apr. 21, 1993, which is a continuation of application No. 07/853,018, Mar. 18, 1992, abandoned, which is a continuation of application No. 07/517,475, May 1, 1990, abandoned, which is a continuation of application No. 07/320,923, Mar. 8, 1989, abandoned, which is a continuation of application No. 06/784,319, Oct. 4, 1985, abandoned, which is a continuation-in-part of application No. 06/699,181, Feb. 5, 1985, abandoned.

[51] Int. Cl.$^7$ .......................... C12N 15/00; C12N 15/63; C07H 21/04
[52] U.S. Cl. ...................... 435/69.2; 536/23.5; 435/320.1
[58] Field of Search ................................ 435/69.2, 252.3, 435/252.31, 252.33, 252.34, 254.2, 254.21, 320.1, 471; 536/23.5

[56] References Cited

U.S. PATENT DOCUMENTS

| | | | |
|---|---|---|---|
| 4,361,574 | 11/1982 | Grant et al. | 514/366 |
| 4,382,081 | 5/1983 | Sundeen et al. | 514/18 |
| 4,394,443 | 7/1983 | Weissman et al. | 435/6 |
| 4,512,922 | 4/1985 | Jones et al. | 530/408 |
| 4,530,901 | 7/1985 | Weissmann et al. | 435/69.51 |
| 4,602,006 | 7/1986 | Krantz et al. | 514/63 |
| 4,609,667 | 9/1986 | Clark et al. | 514/367 |
| 4,897,444 | 1/1990 | Brynes et al. | 525/331 |

FOREIGN PATENT DOCUMENTS

| | | |
|---|---|---|
| 0188-312 | 7/1986 | European Pat. Off. . |
| 0189784 | 8/1986 | European Pat. Off. . |
| 2169295 | 7/1986 | United Kingdom . |

OTHER PUBLICATIONS

Bell et al. (1984) Nature, vol. 310, pp. 775–777.
Smith, M in *Methods of DNA and RNA Sequencing*, pp. 23–68 (Ed. S.M. Weissman), 1983.
Suggs,S. et al, *Proc. Natl. Acad Sci*, vol. 78, pp. 6613–6617, 1981.
Carmichael,D et al, *Proc. Natl Acad Sci*, vol. 83, pp.2407–2411, Apr., 1986.
Watson, M.E.E., "Compilation of published signal sequence," *Nucl. Acids Res.* 12(3):5145–5165 (1984).
Liotta, L.A., "Cancer Cell Invasion and Metastasis," *Scientific American*, pp. 54–63 (Feb. 1992).

Murphy et al., "An Inhibitor of Collagenase From Human Amniotic Fluid: Purification, Characterization and Action on Metaloproteinases," Chemical Abstracts 95: 37942w (1982).
Welgus et al., Collagen Relat. Res., vol. 4, pp. 377–388 (1984).
Murphy et al., Biochimica et Biophysica Acta, 839: 214–218 (1985).
Reynolds et al., "Tissue Metallo–Proteinase Inhibitors and Their Role in Matrix Catabolism," Cellular Interactions, Chapter 16, pp. 205–213 (1981).
Sellers et al., "Rabbit Bone Collagenase Inhibitor Blocks the Activity of Other Neutral Metalloproteinases," Biochemical and Biophysical Research Communications, vol. 87, No. 2, pp. 581–587 (1979).
Murphy et al., "An Inhibitor of Collagenase from Human Amniotic Fluid," Biochem. J., vol. 195, pp. 167–170 (1981).
Cawston et al., "Metalloproteinases and Collagenase Inhibitors in Rheumatoid Synovial Fluid," Arthritis and Rheumatism, vol. 27, No. 3, pp. 285–290 (1984).
Skup, D., et al., Nuc. Acids Res., vol. 10, No. 10, pp. 3069–3084 (1982).
Howard G. Welgus et al., "A Specific Inhibitor of Vertebrate Collagenase Produced by Human Skin Fibroblasts", Journal of Biological Chemistry, vol. 254, No. 6, pp. 1938–1943, Oct. 10, 1982.
Jerome Gross et al., "Collagenolytic Activity In Amphibian Tissues: A Tissue Culture Assay", Physiology, vol. 48, pp. 1014–1022, 1962.
Andrew J.P. Docherty, "Sequence of Human Tissue Inhibitor of Metalloproteinases and Its Identity to Erythroid–potentiating Activity", Nature, vol. 318, pp. 66–69, Nov. 7, 1985.
Judith C. Gasson et al., "Molecular Characterization and Expression of the Gene encoding Human Erythroid–Potentiating Activity", Nature, vol. 315, pp. 768–771, Jun. 27, 1985.
Thomas W. Cooper et al., "Platelet–derived Collagenase Inhibitor: Characterization and Subcellular Localization", Proc. Natl Acad. Sci. USA, vol. 82, pp. 2779–2783, May 1985.
Eugene A. Bauer et al., "Collagenase Production By Human Skin Fibroblasts", Biochemical and Biophysical Research Communications, vol. 64, No. 1, pp. 232–240, 1975.
Roberto Patarca et al., "A Major Retroviral Core Protein Related to EPA and TIMP", Nature, vol. 318, p. 390, 1985.

(List continued on next page.)

*Primary Examiner*—David Guzo
*Assistant Examiner*—Jon Shuman
*Attorney, Agent, or Firm*—Finnegan, Henderson, Farabow, Garrett & Dunner

[57] ABSTRACT

A portable DNA sequence is disclosed which is capable of directing intracellular production of metalloproteinanse inhibitors. Vectors containing this portable DNA sequence are also set forth, including the vector pUC9-F5/237P10 (ATCC Accession No. 53003). A recombinant-DNA method for the microbial production of a metalloproteinase inhibitor, which method incorporates at least one of the portable DNA sequences and the vectors disclosed herein is described.

8 Claims, 1 Drawing Sheet

OTHER PUBLICATIONS

Human Skin Fibroblast Collagenase, Journal of Biological Chemistry, vol. 25, No. 19, pp. 11534–11539, Oct. 10, 1982.

John J. Jeffrey et al., "Studies on the Activation Energy and Deuterium Isotope Effect of Human Skin Collagenase on Homologous Collagen Substrates", Journal of Biological Chemistry, vol. 258, pp. 11123–11127, Sep. 25, 1983.

Howard G. Welgus et al., "The Collagen Substrate Specificity of Rat Uterus Collagenase", Journal of Biological Chemistry, vol. 258, No. 23, pp. 14162–14165, Dec. 10, 1983.

George P. Stricklin et al., "Human skin Fibroblast Collagenase Inhibitor", Journal of Biological Chemistry, vol. 258, No. 20, pp. 12252–12258, Oct. 25, 1983.

Howard G. Welgus, "Human Skin fibroblast Collagenase Inhibitor", Journal of Biological Chemistry, vol. 258, No. 20, pp. 12259–12264, Oct. 25, 1983.

HUMAN COLLAGENASE INHIBITOR SEQUENCE, RECOMBINANT VECTOR SYSTEM FOR USING SAME AND RECOMBINANT-DNA METHOD FOR THE MANUFACTURE OF SAME

This application is a continuation, of application Ser. No. 08/050,739, filed Apr. 21, 1993, which is a continuation application of Ser. No. 07/853,018, filed Mar. 18. 1992, now abandoned, which is a continuation application of Ser. No. 07/517,475, filed May 1, 1990, now abandoned, which is a continuation application of Ser. No. 07/320,923, filed Mar. 8, 1989, now abandoned, which is a continuation application of Ser. No. 06/784,319, filed Oct. 4, 1985, now abandoned, which is a continuation-in-part of Ser. No. 06/699,181, filed Feb. 5, 1985, now abandoned.

BACKGROUND OF THE INVENTION

Endogenous proteolytic enzymes serve to degrade invading organisms, antigen-antibody complexes and certain tissue proteins which are no longer necessary or useful to the organism. In a normally functioning organism, proteolytic enzymes are produced in a limited quantity and are regulated in part through specific inhibitors.

Metalloproteinases are enzymes present in the body which are often involved in the degradation of connective tissue. While some connective tissue degradation is necessary for normal functioning of an organism, an excess of connective tissue degradation occurs in several disease states and is believed to be attributable, at least in part, to excess metalloproteinase. It is believed that metalloproteinases are at least implicated in periodontal disease, corneal and skin ulcers, rheumatoid arthritis and the spread of cancerous solid tumors.

These diseases generally occur in areas of the body which contain a high proportion of collagen, a particular form of connective tissue. An examination of patients with these diseases of connective tissue has revealed an excessive breakdown of the various components of connective tissues, including collagen proteoglycans and elastin. Therefore, it has been deduced that an excessive concentration of a particular metalloproteinase, for example collagenase, proteoglyconuse, gelatinase, and certain elastases, may cause or exacerbate the connective tissue destruction associated with the aforementioned diseases.

In the normal state, the body possesses metalloproteinase inhibitors which bind to metalloproteinases to effectively prevent these enzymes from acting on their connective tissue substrates. Specifically, in a healthy organism, metalloproteinase inhibitors are present in concentrations sufficient to interact with metalloproteinases to an extent which allows sufficient quantities of metalloproteinase to remain active while binding the excess metalloproteinase so that the connective tissue damage seen in the various diseases does not occur.

It is postulated that one immediate cause of the connective tissue destruction present in the foregoing disease states is an imbalance in the relative metalloproteinase/metalloproteinase inhibitor concentrations. In these situations, either due to an excessive amount of active metalloproteinase or a deficiency in the amount of active metalloproteinase inhibitor, the excess metalloproteinase is believed to cause the connective tissue degradation responsible for causing or exacerbating the disease. It is postulated that, by treating persons with connective tissue diseases with metalloproteinase inhibitors, the degradative action of the excess metalloproteinase may be curtailed or halted. Therefore, particular metalloproteinase inhibitors of specific interest to the present inventors are collagenase inhibitors because it is believed that these inhibitors would be pharmaceutically useful in the treatment or prevention of connective tissue diseases.

The existence of metalloproteinase and metalloproteinase inhibitors has been discussed in the scientific literature. For example, Sellers et al., *Biochemical And Biophysical Research Communications* 87:581–587 (1979), discusses isolation of rabbit bone collagenase inhibitor. Collagenase inhibitor isolated from human skin fibroblasts is discussed in Stricklin and Welgus, J. B. C. 258:12252–12258 (1983) and Welgus and Stricklin, J. B. C. 258:12259–12264 (1983). The presence of collagenase inhibitors in naturally-occurring body fluids is further discussed in Murphy et al., Biochem. J. 195:167–170 (1981) and Cawston et al., Arthritis and Rheumatism, 27:285 (1984). In addition, metalloproteinase inhibitors are discussed by Reynolds et al. in *Cellular Interactions*, Dingle and Gordon, eds., (1981). Although these articles characterize particular, isolated metalloproteinase inhibitors and discuss, to some extent, the role or potential role of metalloproteinases in connective tissue disease treatment and speculate on the ability of metalloproteinase inhibitors to counteract this destruction, none of these researchers had previously been able to isolate a portable DNA sequence capable of directing intracellular production of metalloproteinase inhibitors or to create a recombinant-DNA method for the production of these inhibitors.

Surprisingly, the present inventors have discovered a portable DNA sequence capable of directing the recombinant-DNA synthesis of metalloproteinase inhibitors. These metalloproteinase inhibitors are biologically equivalent to those isolated from human skin fibroblast cultures. The metalloproteinase inhibitors of the present invention, prepared by the recombinant-DNA methods set forth herein, will enable increased research into prevention and treatment of metalloproteinase-induced connective tissue diseases. In addition, the metalloproteinase inhibitors of the present invention are useful in neutralizing metalloproleinases, including the excess metalloproteinase associated with disease states. Therefore, it is believed that a cure for these diseases will be developed which will embody, as an active ingredient, the metalloproteinase inhibitors of the present invention. Furthermore, the metalloproteinase inhibitors of the present invention are capable of interacting with their metalloproteinase targets in a manner which allows the development of diagnostic tests for degradative connective tissue diseases using the newly discovered inhibitors.

The recombinant metalloproteinase inhibitors discussed herein interact stoichiometrically (i.e., in a 1:1 ratio) with their metalloproteinase targets. In addition, these metalloproteinase inhibitors are heat resistant, acid stable, glycosylated, and exhibit a high isoelectric point.

SUMMARY OF THE INVENTION

The present invention relates to metalloproteinase inhibitors and a recombinant-DNA method of producing the same and to portable DNA sequences capable of directing intracellular production of the metalloproteinase inhibitors. Particularly, the present invention relates to a collagenase inhibitor, a recombinant-DNA method for producing the same and to portable DNA sequences for use in the recombinant method. The present invention also relates to a series of vectors containing these portable DNA sequences.

One object of the present invention is to provide a metalloproteinase inhibitor, which can be produced in sufficient quantities and purities to provide economical pharmaceutical compositions which possess metalloproteinase inhibitor activity.

An additional object of the present invention is to provide a recombinant-DNA method for the production of these metalloproteinase inhibitors. The recombinant metalloproteinase inhibitors produced by this method are biologically equivalent to the metalloproteinase inhibitor isolable from human skin fibroblast cultures.

To facilitate the recombinant-DNA synthesis of these metalloproteinase inhibitors, it is a further object of the present invention to provide portable DNA sequences capable of directing intracellular production of metalloproteinase inhibitors. It is also an object of the present invention to provide cloning vectors containing these portable sequences. These vectors are capable of being used in recombinant systems to produce pharmaceutically useful quantities of metalloproteinase inhibitors.

Additional objects and advantages of the invention will be set forth in part in the description which follows, and in part will be obvious from the description or may be learned from practice of the invention. The objects and advantages may be realized and attained by means of tne instrumentalities and combinations particularly pointed out in the appended claims.

To achieve the objects and in accordance with the purposes of the present invention, metalloproteinase inhibitors are set forth, which are capable of stoichiometric reaction with metalloproteinases. These metalloproteinase inhibitors are remarkably heat resistant, acid stable, glycosylated, and exhibit a high isoelectric point. Furthermore, these metalloproteinase inhibitors are biologically equivalent to those inhibitors isolated from human skin fibroblast cultures.

To further achieve the objects and in accordance with the purposes of the present invention, as embodied and broadly described herein, portable DNA sequences coding for metalloproteinase inhibitors are provided. These sequences comprise nucleotide sequences capable of directing intracellular production of metalloproteinase inhibitors. The portable sequences may be either synthetic sequences or restriction fragments ("natural" DNA sequences). In a preferred embodiment, a portable DNA sequence is isolated from a human fibroblast cDNA library and is capable of directing intracellular production of a collagenase inhibitor which is biologically equivalent to that inhibitor which is isolable from a human skin fibroblast culture.

The coding strand of a first preferred DNA sequence which has been discovered has the following nucleotide sequence:

```
         10         20         30         40         50         60
GTTGTTGCTG TGGCTGATAG CCCCAGCAGG GCCTGCACCT GTGTCCCACC CCACCCACAG 70         80         90        100        110        120
ACGGCCTTCT GCAATTCCGA CCTCGTCATC AGGGCCAAGT TCGTGGGGAC ACCAGAAGTC 130        140        150        160        170        180
AACCAGACCA CCTTATACCA GCGTTATGAG ATCAAGATGA CCAAGATGTA TAAAGGGTTC 190        200        210        220        230        240
CAAGCCTTAG GGGATGCCGC TGACATCCGG TTCGTCTACA CCCCCGCCAT GGAGAGTGTC 250        260        270        280        290        300
TGCGGATACT TCCACAGGTC CCACAACCGC AGCGAGGAGT TTCTCATTGC TGGAAAACTG 310        320        330        340        350        360
CAGGATGGAC TCTTGCACAT CACTACCTGC AGTTTCGTGG CTCCCTGGAA CAGCCTGAGC 370        380        390        400        410        420
TTAGCTCAGC GCCGGGCTT CACCAAGACC TACACTGTTG GCTGTGAGGA ATGCACAGTG 430        440        450        460        470        480
TTTCCCTGTT TATCCATCCC CTGCAAACTG CAGAGTGGCA CTCATTGCTT GTGGACGGAC 490        500        510        520        530        540
CAGCTCCTCC AAGGCTCTGA AAAGGGCTTC CAGTCCCGTC ACCTTGCCTG CCTGCCTCGG 550        560        570        580        590        600
GAGCCAGGGC TGTGCACCTG GCAGTCCCTG CGGTCCCAGA TAGCCTGAAT CCTGCCCGGA 610        620        630        640        650        660
GTGGAAGCTG AAGCCTGCAC AGTGTCCACC CTGTTCCCAC TCCCATCTTT CTTCCGGACA 670        680        690        700
ATGAAATAAA GAGTTACCAC CCAGCAAAAA AAAAAAGGAA TTC
```

The nucleotides represented by the foregoing abbreviations are set forth in the Detailed Description of the Preferred Embodiments.

A second preferrred DNA sequence has been discovered which has an additional nucleotide sequence 5' to the initiator sequence This sequence, which contains as the eighty-second through four-hundred-thirty-second nucleotides nucleotoides 1 through 351 of the first preferred sequence set forth above, has the following nucleotide sequence:

```
        10         20         30         40         50         60
GGCCATCGCC GCAGATCCAG CGCCCAGAGA GACACCAGAG AACCCACCAT GGCCCCCTTT 70         80         90        100        110        120
GACCCCTGGC TTCTGCATCC TGTTGTTGCT GTGGCTGATA GCCCCAGCAG GGCCTGCACC 130        140        150        160        170        180
TGTGTCCCAC CCCACCCACA GACGGCCTTC TGCAATTCCG ACCTCGTCAT CAGGGCCAAG 190        200        210        220        230        240
TTCGTGGGGA CACCAGAAGT CAACCAGACC ACCTTATACC AGCGTTATGA GATCAAGATG 250        260        270        280        290        300
ACCAAGATGT ATAAAGGGTT CCAAGCCTTA GGGGATGCCG CTGACATCCG GTTCGTCTAC 310        320        330        340        350        360
ACCCCCGCCA TGGAGAGTGT CTGCGGATAC TTCCACAGGT CCCACAACCG CAGCGAGGAG 370        380        390        400        410        420
TTTCTCATTG CTGGAAAACT GCAGGATGGA CTCTTGCACA TCACTACCTG CAGTTTCGTG

430
GCTCCCTGGA AC
```

A third preferred DNA sequence which incorporates the 5' region of the second preferred sequence and the 3' sequence of the first preferred sequence, has the following nucleotide sequence:

```
        10         20         30         40         50         60
GGCCATCGCC GCAGATCCAG CGCCCAGAGA GACACCAGAG AACCCACCAT GGCCCCCTTT 70         80         90        100        110        120
GACCCCTGGC TTCTGCATCC TGTTGTTGCT GTGGCTGATA GCCCCAGCAG GGCCTGCACC 130        140        150        160        170        180
TGTGTCCCAC CCCACCCACA GACGGCCTTC TGCAATTCCG ACCTCGTCAT CAGGGCCAAG 190        200        210        220        230        240
TTCGTGGGGA CACCAGAAGT CAACCAGACC ACCTTATACC AGCGTTATGA GATCAAGATG 250        260        270        280        290        300
ACCAAGATGT ATAAAGGGTT CCAAGCCTTA GGGGATGCCG CTGACATCCG GTTCGTCTAC 310        320        330        340        350        360
ACCCCCGCCA TGGAGAGTGT CTGCGGATAC TTCCACAGGT CCCACAACCG CAGCGAGGAG 370        380        390        400        410        420
TTTCTCATTG CTGGAAAACT GCAGGATGGA CTCTTGCACA TCACTACCTG CAGTTTCGTG 430        440        450        460        470        480
GCTCCCTGGA ACAGCCTGAG CTTAGCTCAG CGCCGGGGCT TCACCAAGAC CTACACTGTT 490        500        510        520        530        540
GGCTGTGAGG AATGCACAGT GTTTCCCTGT TTATCCATCC CCTGCAAACT GCAGAGTGGC 550        560        570        580        590        600
ACTCATTGCT TGTGGACGGA CCAGCTCCTC CAAGGCTCTG AAAAGGGCTT CCAGTCCCGT 610        620        630        640        650        660
CACCTTGCCT GCCTGCCTCG GGAGCCAGGG CTGTGCACCT GGCAGTCCCT GCGGTCCCAG 670        680        690        700        710        720
ATAGCCTGAA TCCTGCCCGG AGTGGAAGCT GAAGCCTGCA CAGTGTCCAC CCTGTTCCCA 730        740        750        760        770        780
CTCCCATCTT TCTTCCGGAC AATGAAATAA AGAGTTACCA CCCAGCAAAA AAAAAAGGA
```

To facilitate identification and isolation of natural DNA sequences for use in the present invention, the inventors have developed a human skin fibroblast cDNA library. This library contains the genetic information capable of directing a cell to synthesize the metalloproteinase inhibitors of the present invention. Other natural DNA sequences which may be used in the recombinant DNA methods set forth herein may be isolated from human genomic libraries.

Additionally, portable DNA sequences useful in the processes of the present invention may be synthetically created. These synthetic DNA sequences may be prepared by polynucleotide synthesis and sequencing techniques known to those of ordinary skill in the art.

Additionally, to achieve the objects and in accordance with the purposes of the present invention, a recombinant-DNA method is disclosed which results in microbial manufacture of the instant metalloproteinase inhibitors using the portable DNA sequences referred to above. This recombinant DNA method comprises:

(a) preparation of a portable DNA sequence capable of directing a host microorganism to produce a protein having metalloproteinase inhibitor activity, preferably collagenase inhibitor activity;

(b) cloning the portable DNA sequence into a vector capable of being transferred into and replicating in a host microorganism, such vector containing operational elements for the portable DNA sequence;

(c) transferring the vector containing the portable DNA sequence and operational elements into a host microorganism capable of expressing the metalloproteinase inhibitor protein;

(d) culturing the host microorganism under conditions appropriate for amplification of the vector and expression of the inhibitor; and (e) in either order:
  (i) harvesting the inhibitor; and
  (ii) causing the inhibitor to assume an active, tertiary structure whereby it possesses metalloproteinase inhibitor activity.

To further accomplish the objects and in further accord with the purposes of the present invention, a series of cloning vectors are provided comprising at least one of the portable DNA sequences discussed above. In particular, plasmid pUC9-F5/237P10 is disclosed.

It is understood that both the foregoing general description and the following detailed description are exemplary and explanatory only and are not restrictive of the invention, as claimed.

The accompanying drawing, which is incorporated in and constitutes a part of this specification, illustrates one embodiment of the invention and, together with the description, serves to explain the principles of the invention.

DETAILED DESCRIPTION OF THE PREFERRED EMBODIMENTS

Figure 1:
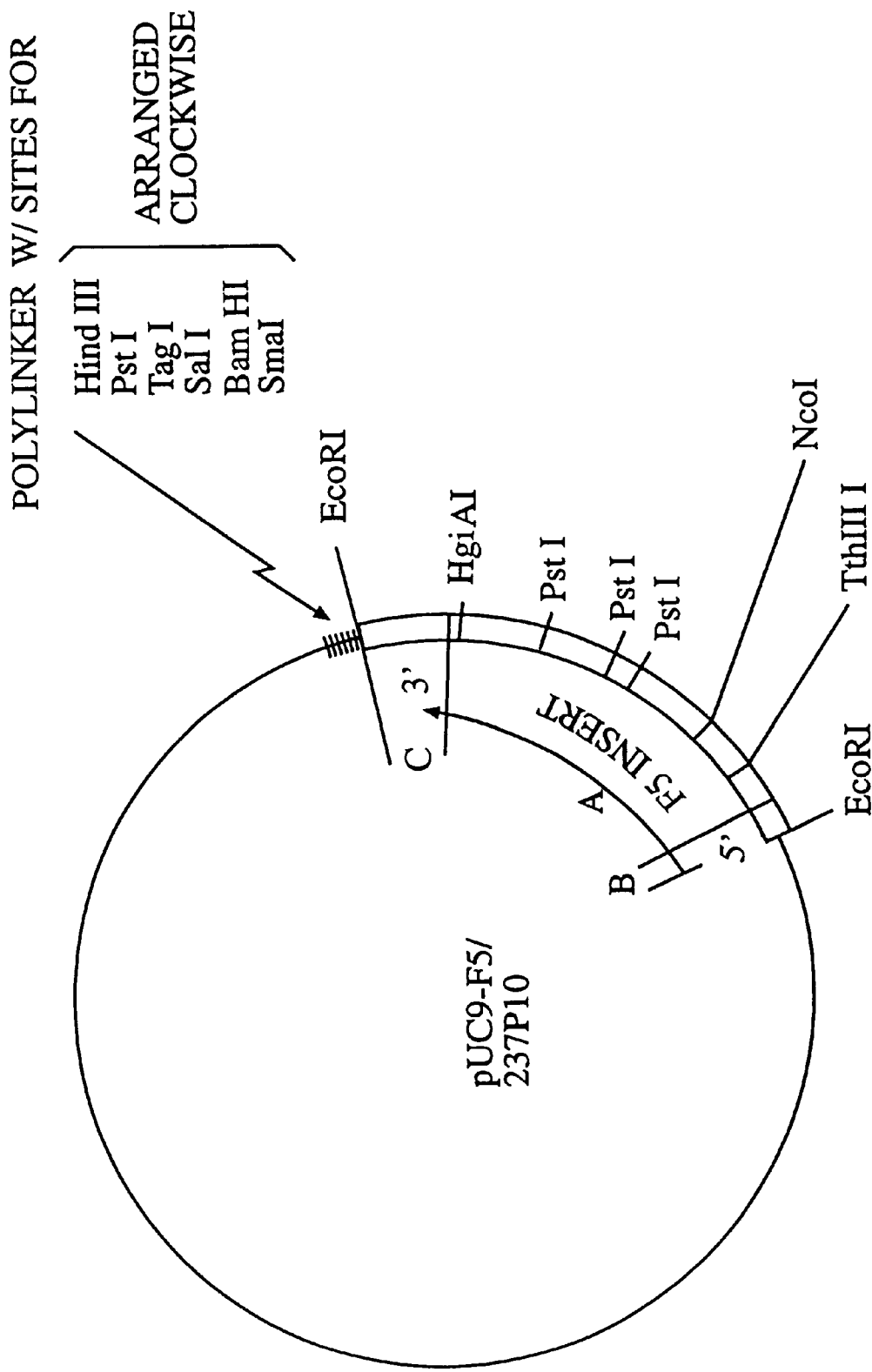
FIG. 1 is a partial restriction map of the plasmid pUC9-F5/237P10.

Reference will now be made in detail to the presently preferred embodiments of the invention, which, together with the drawing and the following examples, serve to explain the principles of the invention.

As noted above, the present invention relates in part to portable DNA sequences capable of directing intracellular production of metalloproteinase inhibitors in a variety of host microorganisms. "Portable DNA sequence" in this context is intended to refer either to a synthetically-produced nucleotide sequence or to a restriction fragment of a naturally occuring DNA sequence. For purposes of this specification, "metalloproteinase inhibitor" is intended to mean the primary structure of the protein as defined by the codons present in the deoxyribonucleic acid sequence which directs intracellular production of the amino acid sequence, and which may or may not include post-translational modifications. It is contemplated that such post-translational modifications include, for example, glycosylation. It is further intended that the term "metalloproteinase inhibitor" refer to either the form of the protein as would be excreted from a microorganism or the methionyl-metalloproteinase inhibitor as it may be present in microorganisms from which it was not excreted.

In a preferred embodiment, the portable DNA sequences are capable of directing intracellular production of collagenase inhibitors. In a particularly preferred embodiment, the portable DNA sequences are capable of directing intracellular production of a collagenase inhibitor biologically equivalent to that previously isolated from human skin fibroblast cultures. By "biologically equivalent", as used herein in the specification and claims, it is meant that an inhibitor, produced using a portable DNA sequence of the present invention, is capable of preventing collagenase-induced tissue damage of the same type, but not necessarily to the same degree, as a native human collagenase inhibitor, specifically that native human collagenase inhibitor isolable from human skin fibroblast cell cultures.

A first preferred portable DNA sequence of the present invention has a nucleotide sequence as follows:

```
            10         20         30         40         50         60
     GTTGTTGCTG TGGCTGATAG CCCCAGCAGG GCCTGCACCT GTGTCCCACC CCACCCACAG 70         80         90        100        110        120
     ACGGCCTTCT GCAATTCCGA CCTCGTCATC AGGGCCAAGT TCGTGGGGAC ACCAGAAGTC 130        140        150        160        170        180
     AACCAGACCA CCTTATACCA GCGTTATGAG ATCAAGATGA CCAAGATGTA TAAAGGGTTC 190        200        210        220        230        240
     CAAGCCTTAG GGGATGCCGC TGACATCCGG TTCGTCTACA CCCCCGCCAT GGAGAGTGTC 250        260        270        280        290        300
     TGCGGATACT TCCACAGGTC CCACAACCGC AGCGAGGAGT TTCTCATTGC TGGAAAACTG 310        320        330        340        350        360
     CAGGATGGAC TCTTGCACAT CACTACCTGC AGTTTCGTGG CTCCCTGGAA CAGCCTGAGC 370        380        390        400        410        420
     TTAGCTCAGC GCCGGGGCTT CACCAAGACC TACACTGTTG GCTGTGAGGA ATGCACAGTG 430        440        450        460        470        480
     TTTCCCTGTT TATCCATCCC CTGCAAACTG CAGAGTGGCA CTCATTGCTT GTGGACGGAC 490        500        510        520        530        540
     CAGCTCCTCC AAGGCTCTGA AAAGGGCTTC CAGTCCCGTC ACCTTGCCTG CCTGCCTCGG
```

```
            550        560        570        580        590        600
       GAGCCAGGGC TGTGCACCTG GCAGTCCCTG CGGTCCCAGA TAGCCTGAAT CCTGCCCGGA 610        620        630        640        650        660
       GTGGAAGCTG AAGCCTGCAC AGTGTCCACC CTGTTCCCAC TCCCATCTTT CTTCCGGACA 670        680        690        700
       ATGAAATAAA GAGTTACCAC CCAGCAAAAA AAAAAAGGAA TTC
``` wherein the following nucleotides are represented by the abbreviations indicated below.

| Nucleotides | Abbreviation |
|---|---|
| Deoxyadenlic acid | A |
| Deoxyguanylic acid | G |
| Deoxycytidylic acid | C |
| Thymidylic acid | T |

A second preferred portable DNA sequence of the present invention has the following nucleotide sequence:

```
     10         20         30         40         50         60
GGCCATCGCC GCAGATCCAG CGCCCAGAGA GACACCAGAG AACCCACCAT GGCCCCCTTT 70         80         90        100        110        120
GACCCCTGGC TTCTGCATCC TGTTGTTGCT GTGGCTGATA GCCCCAGCAG GGCCTGCACC 130        140        150        160        170        180
TGTGTCCCAC CCCACCCACA GACGGCCTTC TGCAATTCCG ACCTCGTCAT CAGGGCCAAG 190        200        210        220        230        240
TTCGTGGGGA CACCAGAAGT CAACCAGACC ACCTTATACC AGCGTTATGA GATCAAGATG 250        260        270        280        290        300
ACCAAGATGT ATAAAGGGTT CCAAGCCTTA GGGGATGCCG CTGACATCCG GTTCGTCTAC 310        320        330        340        350        360
ACCCCCGCCA TGGAGAGTGT CTGCGGATAC TTCCACAGGT CCCACAACCG CAGCGAGGAG 370        380        390        400        410        420
TTTCTCATTG CTGGAAAACT GCAGGATGGA CTCTTGCACA TCACTACCTG CAGTTTCGTG

430
GCTCCCTGGA AC
```

In this second preferred sequence, an open reading frame exists from nucleotides 1 through 432. The first methionine of this reading frame is encoded by nucleotides by 49 through 51 and is the site of translation initiation. It should be noted that the amino acid sequence prescribed nucleotides 49 through 114 is not found in the mature metalloproteinase. It is believed that this sequence is the leader peptide of the human protein.

A third preferred portable DNA sequence has the mucleotide sequence:

```
     10         20         30         40         50         60
GGCCATCGCC GCAGATCCAG CGCCCAGAGA GACACCAGAG AACCCACCAT GGCCCCCTTT 70         80         90        100        110        120
GACCCCTGGC TTCTGCATCC TGTTGTTGCT GTGGCTGATA GCCCCAGCAG GGCCTGCACC 130        140        150        160        170        180
TGTGTCCCAC CCCACCCACA GACGGCCTTC TGCAATTCCG ACCTCGTCAT CAGGGCCAAG 190        200        210        220        230        240
TTCGTGGGGA CACCAGAAGT CAACCAGACC ACCTTATACC AGCGTTATGA GATCAAGATG 250        260        270        280        290        300
ACCAAGATGT ATAAAGGGTT CCAAGCCTTA GGGGATGCCG CTGACATCCG GTTCGTCTAC 310        320        330        340        350        360
ACCCCCGCCA TGGAGAGTGT CTGCGGATAC TTCCACAGGT CCCACAACCG CAGCGAGGAG
```

-continued

```
         370        380        390        400        410        420
    TTTCTCATTG CTGGAAAACT GCAGGATGGA CTCTTGCACA TCACTACCTG CAGTTTCGTG 430        440        450        460        470        480
    GCTCCCTGGA ACAGCCTGAG CTTAGCTCAG CGCCGGGGCT TCACCAAGAC CTACACTGTT 490        500        510        520        530        540
    GGCTGTGAGG AATGCACAGT GTTTCCCTGT TTATCCATCC CCTGCAAACT GCAGAGTGGC 550        560        570        580        590        600
    ACTCATTGCT TGTGGACGGA CCAGCTCCTC CAAGGCTCTG AAAAGGGCTT CCAGTCCCGT 610        620        630        640        650        660
    CACCTTGCCT GCCTGCCTCG GGAGCCAGGG CTGTGCACCT GGCAGTCCCT GCGGTCCCAG 670        680        690        700        710        720
    ATAGCCTGAA TCCTGCCCGG AGTGGAAGCT GAAGCCTGCA CAGTGTCCAC CCTGTTCCCA 730        740        750        760        770        780
    CTCCCATCTT TCTTCCGGAC AATGAAATAA AGAGTTACCA CCCAGCAAAA AAAAAAAGGA
```

This third sequence contains the 5' nontranslated region of the second preferred sequence and the 3' region of the first preferred sequence. It is envisioned that this third preferred sequence is capable of directing intracellular production of a metalloproteinase analogous to a mature human collagenase inhibitor in a microbial or mammalian expression system.

It must be borne in mind in the practice of the present invention that the alteration of some amino acids in a protein sequence may not affect the fundamental properties of the protein. Therefore, it is also contemplated that other portable DNA sequences, both those capable of directing intracellular production of identical amino acid sequences and those capable of directing intracellular production of analogous amino acid sequences which also possess metalloproteinase inhibitor activity, are included within the ambit of the present invention.

It is contemplated that some of these analogous amino acid sequences will be substantially homologous to native human metalloproteinase inhibitors while other amino acid sequences, capable of functioning as metalloproteinase inhibitors, will not exhibit substantial homology to native inhibitors. By "substantial homology", as used herein, is meant a degree of homology to a native metalloproteinase inhibitor in excess of 50%, preferably in excess of 60%, preferably in excess of 80%. The percentage homology as discussed herein is calculated as the percentage of amino acid residues found in the smaller of the two sequences that align with identical amino acid residues in the sequence being compared when four gaps in a length of 100 amino acids may be introduced to assist in that alignment as set forth by Dayhoff, M. O. in *Atlas of Protein Sequence and Structure* Vol. 5, p. 124 (1972), National Biochemical Research Foundation, Washington, D.C., specifically incorporated herein by reference.

As noted above, the portable DNA sequences of the present invention may be synthetically created. It is believed that the means for synthetic creation of these polynucleotide sequences are generally known to one of ordinary skill in the art, particularly in light of the teachings contained herein. As an example of the current state of the art relating to polynucleotide synthesis, one is directed to Matteucci, M. D. and Caruthers, M. H., in J. Am. Chem. Soc. 103: 3185 (1981) and Beaucage, S. L. and Caruthers, M. H. in Tetrahedron Lett. 22: 1859 (1981), specifically incorporated herein by reference.

Additionally, the portable DNA sequence may be a fragment of a natural sequence, i.e., a fragment of a polynucleotide which occurred in nature and which has been isolated and purified for the first time by the present inventors. In one embodiment, the portable DNA sequence is a restriction fragment isolated from a cDNA library. In this preferred embodiment, the cDNA library is created from human skin fibroblasts.

In an alternative embodiment, the portable DNA sequence is isolated from a human genomic library. An example of such a library useful in this embodiment is set forth in Lawn et al. Cell 15: 1157–1174 (1978), specifically incorporated herein by reference.

As also noted above, the present invention relates to a series of vectors, each containing at least one of the portable DNA sequences described herein. It is contemplated that additional copies of the portable DNA sequence may be included in a single vector to increase a host microorganism's ability to produce large quantities of the desired metalloproteinase inhibitor.

In addition, the cloning vectors within the scope of the present invention may contain supplemental nucleotide sequences preceding or subsequent to the portable DNA sequence. These supplemental sequences are those that will not interfere with transcription of the portable DNA sequence and will, in some instances as set forth more fully hereinbelow, enhance transcription, translation, or the ability of the primary amino acid structure of the resultant metalloproteinase inhibitor to assume an active, tertiary form.

A preferred vector of the present invention is set forth in FIG. 1. This vector, pUC9-F5/237P10, contains the preferred nucleotide sequence set forth above. Vector pUC9-F5/237P10 is a plasmid present in C600/pUC9-F5/237P10 cells. Those cells were deposited on Jan. 23, 1985, with the American Type Culture Collection, 10801 University Boulevard, Manassas, Va. 20110-2209, under ATCC Accession No. 53003.

The deposit was made on Jan.23, 1985 with the American Type Culture Collection (ATCC).

A preferred nucleotide sequence encoding the metalloproteinase inhibitor is identified in FIG. 1 as region A. Plasmid pUC9-F5/237P10 also contains supplemental nucleotide sequences preceding and subsequent to the preferred portable DNA sequence in region A. These supplemental sequences are identified as regions B and C, respectively.

In alternate preferred embodiments, either one or both of the preceding or subsequent supplemental sequences may be removed from the vector of FIG. 1 by treatment of the vector with restriction endonucleases appropriate for removal of the supplemental sequences. The supplemental sequence subsequent to the portable DNA sequence, identified in FIG.

1 as region C, may be removed by treatment of the vector with a suitable restriction endonuclease, preferably HqiAI followed by reconstruction of the 3' end of region A using synthetic oligonucleotides and ligation of the vector with T-4 DNA ligase. Deletion of the supplemental sequence preceding the portable DNA sequence, identified as region B in FIG. 1, would be specifically accomplished by the method set forth in Example 2.

In preferred embodiments, cloning vectors containing and capable of expressing the portable DNA sequence of the present invention contain various operational elements. These "operational elements," as discussed herein, include at least one promoter, at least one Shine-Dalgarno sequence, at least one terminator codon. Preferably, these "operational elements" also include at least one operator, at least one leader sequence, and for proteins to be exported from intracellular space, at least one regulator and any other DNA sequences necessary or preferred for appropriate transcription and subsequent translation of the vector DNA.

Additional embodiments of the present invention are envisioned as employing other known or currently undiscovered vectors which would contain one or more of the portable DNA sequences described herein. In particular, it is preferred that these vectors have some or all of the following characteristics: (1) possess a minimal number of host-organism sequences; (2) be stable in the desired host; (3) be capable of being present in a high copy number in the desired host; (4) possess a regulatable promoter; (5) have at least one DNA sequence coding for a selectable trait present on a portion of the plasmid separate from that where the portable DNA sequence will be inserted; and (6) be integrated into the vector.

The following, noninclusive, list of cloning vectors is believed to set forth vectors which can easily be altered to meet the above-criteria and are therefore preferred for use in the present invention. Such alterations are easily performed by those of ordinary skill in the art in light of the available literature and the teachings herein.

TABLE I

| HOST | Vectors | Comments |
|---|---|---|
| E. coli | pUC8 | Many selectable replicons |
| | pUC9 | have been characterized. |
| | pBR322 | Maniatis, T. et al. (1982), |
| | pGW7 | Molecular Cloning: A |
| | placI$^q$ | Laboratory Manual, Cold |
| | pDP8 | Spring Harbor Laboratory. |
| BACILLUS | pUB110 | Genetics and Biotechnology |
| B. subtilis | pSA0501 | of Bacilli, Ganesan and |
| B. amyloliquefaciens | pSA2100 | Hoch, eds., 1984, Academic |
| B. stearothermophilus | pBD6 | Press. |
| | pBD8 | |
| | pT127 | |
| PSEUDOMONAS | RSF1010 | Some vectors useful in |
| P. aeruginosa | Rmsl49 | broad host range of gram- |
| P. putida | pKT209 | negative bacteria including |
| | RK2 | Xanthomonas and Agrobacterium. |
| | pSa727 | |
| CLOSTRIDIUM | pJU12 | Shuttle plasmids for E. |
| C. perfringens | pJU7 | coli and C. perfringens |
| | pJU10 | construction ref. Squires, |
| | pJU16 | C. et al. (1984) Journal |
| | pJU13 | Bacteriol. 159:465-471. |
| SACCHAROMYCES | YEp24 | Botstein and Davis in |
| S. cerevisiae | YIp5 | Molecular Biology of the |
| | YRp17 | Yeast Saccharomyces, |
| | | Strathern, Jones, and |
| | | Broach, eds., 1982, Cold |
| | | Spring Harbor Laboratory. |

It is to be understood that additional cloning vectors may now exist or will be discovered which have the above-identified properties and are therefore suitable for use in the present invention. These vectors are also contemplated as being within the scope of the disclosed series of cloning vectors into which the portable DNA sequences may be introduced, along with any necessary operational elements, and which altered vector is then included within the scope of the present invention and-would be capable of being used in the recombinant-DNA method set forth more fully below.

In addition to the above list, an *E. coli* vector system, as set forth in Example 2, is preferred in one embodiment as a cloning vector. Moreover, several vector plasmids which autonomously replicate in a broad range of Gram Negative bacteria are preferred for use as cloning vehicles in hosts of the genera Pseudomonas. These are described by Tait, R. C., Close, T. J., Lundquist, R. C., Hagiya, M., Rodriguez, R. L., and Kado, C. I. in Biotechnology, May, 1983, pp. 269–275; Panopoulos, N. J. in *Genetic Engineering in the Plant Sciences*, Praeger Publishers, New York, N.Y., pp. 163–185, (1981); and Sakaguchi, K. in Current Topic in Microbiology and Immunology 96:31–45, (1982), each of which is specifically incorporated herein by reference.

One particularly preferred construction employs the plasmid RSF1010 and derivatives thereof as described by Bagdasarian, M., Bagdasarian, M. M., Coleman, S., and Timmis, K. N. in *Plasmids of Medical Environmental and Commercial Importance*, Timmis, K. N. and Puhler, A. eds., Elsevier/North Holland Biomedical Press, (1979), specifically incorporated herein by reference. The advantages of RSF1010 are that it is relatively small, high copy number plasmid which is readily transformed into and stably maintained in both *E. coli* and Pseudomonas species. In this system, it is preferred to use the Tac expression system as described for Escherichia, since it appears that the *E. coli* trp promoter is readily recognized by Pseudomonas RNA polymerase as set forth by Sakaguchi, K. in Current Topics in Microbiology and Immunology 96:31–45 (1982) and Gray, G. L., McKeown, K. A., Jones, A. J. S., Seeburg, P. H., and Heyneker, H. L. in Biotechnology Feb. 1984, pp. 161–165, both of which are specifically incorporated herein by reference. Transcriptional activity may be further maximized by requiring the exchange of the promoter with, e.g., an *E. coli* or *P. aeruginosa* trp promoter.

In a preferred embodiment, *P. aeruginosa* is transformed with vectors directing the synthesis of the metalloproteinase inhibitor as either an intracellular product or as a product coupled to leader sequences that will effect its processing and export from the cell. In this embodiment, these leader sequences are preferably selected from the group consisting of beta-lactamase, OmpA protein, the naturally occurring human signal peptide, and that of carboxyeptidase G2 from Pseudomonas. Translation may be coupled to translation initiation for any of the *E. coli* proteins as described in Example 2, as well as to initiation sites for any of the highly expressed proteins of the host to cause intracellular expression of the metalloproteinase inhibitor.

In those cases where restriction minus strains of a host Pseudomonas species are not available, transformation efficiency with plasmid constructs isolated from *E. coli* are poor. Therefore, passage of the Pseudomonas cloning vector through an r−m+ strain of another species prior to transformation of the desired host, as set forth in Bagdasarian, M., et al., *Plasmids of Medical, Environmental and Commercial Importance*, pp. 411–422, Timmis and Puhler eds., Elsevier/North Holland Biomedical Press (1979), specifically incorporated herein by reference, is desired.

Furthermore, a preferred expression system in hosts of the genera Bacillus involves using plasmid pUB110 as the cloning vehicle. As in other host vector systems, it is possible in Bacillus to express the metalloproteinase inhibitors of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering*, Vol. 2, Setlow and Hollander eds., Plenum Press, New York, N.Y., pp. 115–131, (1980), specifically incorporated herein by reference. For the expression and secretion of metalloproteinase inhibitors from *B. subtilis*, the signal sequence of alpha-amylase is preferably coupled to the coding region for the metalloproteinase inhibitor. For synthesis of intracellular metalloproteinase inhibitor, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilli*, Ganesan, A. T. and Hoch, J. A., eds., Academic Press, pp. 249–263, (1984), specifically incorporated by reference. The lacI gene of lacI$^q$ would also be included to effect regulation.

One preferred construction for expression in Clostridium is in plasmid pJU12 described by Squires, C. H. et al in J. Bacteriol. 159:465–471 (1984), specifically incorporated herein by reference, transformed into *C. perfringens* by the method of Heefner, D. L. et al. as described in J. Bacteriol. 159:460–464 (1984), specifically incorporated herein by reference.

Transcription is directed by the promoter of the tetracycline resistance gene. Translation is coupled to the Shine-Dalgarno sequences of this same tet$^r$ gene in a manner strictly analogous to the procedures outlined above for vectors suitable for use in other hosts.

Maintenance of foreign DNA introduced into yeast can be effected in several ways (Botstein, D., and Davis, R. W., in *The Molecular Biology of the Yeast Saccharomyces*, Cold Spring Harbor Laboratory, Strathern, Jones and Broach, eds., pp. 607–636 (1982). One preferred expression system for use with host organisms of the genus Saccharomyces harbors the anticollagenase gene on the 2 micron plasmid. The advantages of the 2 micron circle include relatively high copy number and stability when introduced into cir° strains. These vectors perferably incorporate the replication origin and at least one antibiotic resistance marker from pBR322 to allow replication and selection in *E. coli*. In addition, the plasmid will preferably have 2 micron sequences and the yeast LEU2 gene to serve the same purposes in LEU2 mutants of yeast.

The regulatable promoter from the yeast GALL gene will preferably be adapted to direct transcription of the portable DNA sequence gene. Translation of the portable DNA sequence in yeast will be coupled to the leader sequence that directs the secretion of yeast alpha-factor. This will cause formation of a fusion protein which will be processed in yeast and result in secretion of a metalloproteinase inhibitor. Alternatively, a methionylmetalloproteinase inhibitor will be translated for inclusion within the cell.

It is anticipated that translation of mRNA coding for the metalloproteinase inhibitor in yeast will be more efficient with the preferred codon usage of yeast than with the sequence present in pUC8-Fic, as identified in Example 2, which has been tailored to the prokaryotic bias. For this reason, the portion of the 5' end of the portable DNA sequence beginning at the TthlllI site is preferably resynthesized. The new sequence favors the codons most frequently used in yeast. This new sequence preferably has the following nucleotide sequence:

```
           HgiAI
5' GAT CCG TGC ACT TGT GTT CCA CCA CAC
       GC ACG TGA ACA CAA GGT GGT GTG

CCA CAA ACT GCT TTC TGT AAC TCT GAC C
   GGT GTT TGA CGA AAG ACA TTG AGA CTG GA 3'
```

As will be seen from an examination of the individual cloning vectors and systems contained on the above list and description, various operational elements may be present in each of the preferred vectors of the present invention. It is contemplated any additional operational elements which may be required may be added to these vectors using methods known to those of ordinary skill in the art, particularly in light of the teachings herein.

In practice, it is possible to construct each of these vectors in a way that allows them to be easily isolated, assembled, and interchanged. This facilitates assembly of numerous functional genes from combinations of these elements and the coding region of the metalloproteinase inhibitor. Further, many of these elements will be applicable in more than one host.

At least one origin of replication recognized by the contemplated host microorganism, along with at least one selectable marker and at least one promoter sequence capable of initiating transcription of the portable DNA sequence are contemplated as being included in these vectors. It is additionally contemplated that the vectors, in certain preferred embodiments, will contain DNA sequences capable of functioning as regulators ("operators"), and other DNA sequences capable of coding for regulator proteins. In preferred vectors of this series, the vectors additionally contain ribosome binding sites, transcription terminators and leader sequences.

These regulators, in one embodiment, will serve to prevent expression of the portable DNA sequence in the presence of certain environmental conditions and, in the presence of other environmental conditions, allow transcription and subsequent expression of the protein coded for by the portable DNA sequence. In particular, it is preferred that regulatory segments be inserted into the vector such that expression of the portable DNA sequence will not occur in the absence of, for example, isopropylthio-β-galactoside. In this situation, the transformed microorganisms containing the portable DNA may be grown to a desired density prior to initiation of the expression of the metalloproteinase inhibitor. In this embodiment, expression of the desired protease inhibitor is induced by addition of a substance to the microbial environment capable of causing expression of the DNA sequence after the desired density has been achieved.

Additionally, it is preferred that an appropriate secretory leader sequence be present, either in the vector or at the 5' end of the portable DNA sequence, the leader sequence being in a position which allows the leader sequence to be immediately adjacent to the initial portion of the nucleotide sequence capable of directing expression of the protease inhibitor without any intervening transcription or translation termination signals. The presence of the leader sequence is desired in part for one or more of the following reasons: 1) the presence of the leader sequence may facilitate host processing of the initial product to the mature recombinant metalloproteinase inhibitor; 2) the presence of the leader sequence may facilitate purification of the recombinant metalloproteinase inhibitors, through directing the metalloproteinase inhibitor out of the cell cytoplasm; 3) the presence of the leader sequence may affect the ability of the recombinant metalloproteinase inhibitor to fold to its active structure through directing the metalloproteinase inhibitor out of the cell cytoplasm.

In particular, the leader sequence may direct cleavage of the initial translation product by a leader peptidase to remove the leader sequence and leave a polypeptide with the amino acid sequence which has the potential of metalloproteinase inhibitory activity. In some species of host microorganisms, the presence of the appropriate leader sequence will allow transport of the completed protein into the periplasmic space, as in the case of *E. coli*. In the case of certain yeasts and strains of Bacillus and Pseudomonas, the appropriate leader sequence will allow transport of the protein through the cell membrane and into the extracellular medium. In this situation, the protein may be purified from extracellular protein.

Thirdly, in the case of some of the metalloproteinase inhibitors prepared by the present invention, the presence of the leader sequence may be necessary to locate the completed protein in an environment where it may fold to assume its active structure, which structure possesses the appropriate metalloproteinase activity.

Additional operational elements include, but are not limited to, ribosome-binding sites and other DNA sequences necessary for microbial expression of foreign proteins. The operational elements as discussed herein can be routinely selected by those of ordinary skill in the art in light of prior literature and the teachings contained herein. General examples of these operational elements are set forth in B. Lewin, *Genes*, Wiley & Sons, New York (1983), which is specifically incorporated herein by reference. Various examples of suitable operational elements may be found on the vectors discussed above and may be elucidated through review of the publications discussing the basic characteristics of the aforementioned vectors.

In one preferred embodiment of the present invention, an additional DNA sequence is located immediately preceding the portable DNA sequence which codes for the metalloproteinase inhibitor. The additional DNA sequence is capable of functioning as a translational coupler, i.e., it is a DNA sequence that encodes an RNA which serves to position ribosomes immediately adjacent to the ribosome binding site of the metalloproteinase inhibitor RNA with which it is contiguous.

Upon synthesis and/or isolation of all necessary and desired component parts of the above-discussed cloning vectors, the vectors are assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth in Schoner et al., Proceedings of the National Academy of Sciences U.S.A., 81:5403–5407 (1984), which is specifically incorporated herein by reference.

In construction of the cloning vectors of the present invention, it should additionally be noted that multiple copies of the portable DNA sequence and its attendant operational elements may be inserted into each vector. In such an embodiment, the host organism would produce greater amounts per vector of the desired metalloproteinase inhibitor. The number of multiple copies of the DNA sequence which may be inserted into the vector is limited only by the ability of the resultant vector, due to its size, to be transferred into and replicated and transcribed in an appropriate host microorganism.

Additionally, it is preferred that the cloning vector contain a selectable marker, such as a drug resistance marker or other marker which causes expression of a selectable trait by the host microorganism. In a particularly preferred embodiment of the present invention, the gene for ampicillin resistance is included in vector pUC9-F5/237P10.

Such a drug resistance or other selectable marker is intended in part to facilitate in the selection of transformants. Additionally, the presence of such a selectable marker on the cloning vector may be of use in keeping contaminating microorganisms from multiplying in the culture medium. In this embodiment, such a pure culture of the transformed host microorganisms would be obtained by culturing the microorganisms under conditions which require the induced phenotype for survival.

It is noted that, in preferred embodiment, it is also desirable to reconstruct the 3' end of the coding region to allow assembly with 3' non-translated sequences. Included among these non-translated sequences are those which stabilize the mRNA or enhance its transcription and those that provide strong transcriptional termination signals which may stabilize the vector as they are identified by Gentz, R., Langner, A., Chang, A. C. Y., Cohen, S. H., and Bujard, H. in Proc. Natl. Acad. Sci. USA 78:4936–4940 (1981), specifically incorporated herein by reference.

This invention also relates to a recombinant-DNA method for the production of metallproteinase inhibitors. Generally, this method includes:

(a) preparation of a portable DNA sequence capable of directing a host microorganism to produce a protein having metalloproteinase inhibitor activity;

(b) cloning the portable DNA sequence into a vector capable of being transferred into and replicating in a host microorganism, such vector containing operational elements for the portable DNA sequence;

(c) transferring the vector containing the portable DNA sequence and operational elements into a host microorganism capable of expressing the metalloproteinase inhibitor protein;

(d) culturing the host microorganism under conditions appropriate for amplification of the vector and expression of the inhibitor; and (e) in either order:
  (i) harvesting the inhibitor; and
  (ii) causing the inhibitor to assume an active, tertiary structure whereby it possesses metalloproteinase inhibitor activity.

In this method, the portable DNA sequences are those synthetic or naturally-occurring polynucleotides described above. In a preferred embodiment of the present method, the portable DNA sequence has the nucleotide sequence as follows:

```
        10         20         30         40         50         60
GTTGTTGCTG TGGCTGATAG CCCCAGCAGG GCCTGCACCT GTGTCCCACC CCACCCACAG 70         80         90        100        110        120
ACGGCCTTCT GCAATTCCGA CCTCGTCATC AGGGCCAAGT TCGTGGGGAC ACCAGAAGTC 130        140        150        160        170        180
AACCAGACCA CCTTATACCA GCGTTATGAG ATCAAGATGA CCAAGATGTA TAAAGGGTTC 190        200        210        220        230        240
CAAGCCTTAG GGGATGCCGC TGACATCCGG TTCGTCTACA CCCCCGCCAT GGAGAGTGTC 250        260        270        280        290        300
TGCGGATACT TCCACAGGTC CCACAACCGC AGCGAGGAGT TTCTCATTGC TGGAAAACTG 310        320        330        340        350        360
CAGGATGGAC TCTTGCACAT CACTACCTGC AGTTTCGTGG CTCCCTGGAA CAGCCTGAGC 370        380        390        400        410        420
TTAGCTCAGC GCCGGGCTT CACCAAGACC TACACTGTTG GCTGTGAGGA ATGCACAGTG 430        440        450        460        470        480
TTTCCCTGTT TATCCATCCC CTGCAAACTG CAGAGTGGCA CTCATTGCTT GTGGACGGAC 490        500        510        520        530        540
CAGCTCCTCC AAGGCTCTGA AAAGGGCTTC CAGTCCCGTC ACCTTGCCTG CCTGCCTCGG 550        560        570        580        590        600
GAGCCAGGGC TGTGCACCTG GCAGTCCCTG CGGTCCCAGA TAGCCTGAAT CCTGCCCGGA 610        620        630        640        650        660
GTGGAAGCTG AAGCCTGCAC AGTGTCCACC CTGTTCCCAC TCCCATCTTT CTTCCGGACA 670        680        690        700
ATGAAATAAA GAGTTACCAC CCAGCAAAAA AAAAAAGGAA TTC
```

The vectors contemplated as being useful in the present method are those described above. In a preferred embodiment, the cloning vector pUC9-F5/237P10 is used in the disclosed method.

The vector thus obtained is then transferred into the appropriate host microorganism. It is believed that any microorganism having the ability to take up exogenous DNA and express those genes and attendant operational elements may be chosen. It is preferred that the host microorganism be an anaerobe, facultative anaerobe aerobe. Particular hosts which may be preferable for use in this method include yeasts and bacteria. Specific yeasts include those of the genus Saccharomyces, and especially *Saccharomyces cerevisiae*.

Specific bacteria include those of the genera Bacillus and Escherichia and Pseudomonas. Various other preferred hosts are set forth in Table I, supra. In other, alternatively preferred embodiments of the present invention, *Bacillus subtilis, Escherichia coli* or *Pseudomonas aeruginosa* are selected as the host microorganisms.

After a host organism has been chosen, the vector is transferred into the host organism using methods generally known by those of ordinary skill in the art. Examples of such methods may be found in *Advanced Bacterial Genetics* by R. W. Davis et al., Cold Spring Harbor Press, Cold Spring Harbor, N.Y., (1980), which is specifically incorporated herein by reference. It is preferred, in one embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the synthetic genes.

If it is contemplated that the recombinant metalloproteinase inhibitors will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of the metalloproteinase inhibitor.

The host microorganisms are cultured under conditions appropriate for the expression of the metalloproteinase inhibitor. These conditions are generally specific for the host organism, and are readily determined by one of ordinary skill in the art, in light of the published literature regarding the growth conditions for such organisms, for example *Bergey's Manual of Determinative Bacteriology*, 8th Ed., Williams & Wilkins Company, Baltimore, Md., which is specifically incorporated herein by reference.

Any conditions necessary for the regulation of the expression of the DNA sequence, dependent upon any operational elements inserted into or present in the vector, would be in effect at the transformation and culturing stages. In one embodiment, the cells are grown to a high density in the presence of appropriate regulatory conditions which inhibit the expression of the DNA sequence. When optimal cell density is approached, the environmental conditions are altered to those appropriate for expression of the portable DNA sequence. It is thus contemplated that the production of the metalloproteinase inhibitor will occur in a time span subsequent to the growth of the host cells to near optimal density, and that the resultant metalloproteinase inhibitor will be harvested at some time after the regulatory conditions necessary for its expression were induced.

In a preferred embodiment of the present invention, the recombinant metalloproteinase inhibitor is purified subsequent to harvesting and prior to assumption of its active structure. This embodiment is preferred as the inventors believe that recovery of a high yield of re-folded protein is facilitated if the protein is first purified. However, in one preferred, alternate embodiment, the metalloproteinase inhibitor may be allowed re-fold to assume its active structure prior to purification. In yet another preferred, alternate embodiment, the metalloproteinase inhibitor is caused to assume its re-folded, active state upon recovery from the culturing medium.

In certain circumstances, the metalloproteinase inhibitor will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein. The preferred metalloproteinase inhibitors of the present invention will assume their mature, active form upon translocation out of the inner cell membrane. The structures of numerous signal peptides have been published, for example by Marion E. E. Watson in Nuc. Acid Res. 12:515–5164, 1984, specifically incorporated herein by reference. It is intended that these leader sequences, together with portable DNA, will direct intracellular production of a fusion protein which will be transported through the cell membrane and will have the leader sequence portion cleaved upon release from the cell.

In a preferred embodiment, the signal peptide of the *E.coli* OmpA protein is used as a leader sequence and is located in a position contiguous with the portable DNA sequence coding for the metalloproteinese inhibitor structure.

Additionally preferred leader sequences include those of beta-lactamase, carboxypeptidase G2 and the human signal protein. These and other leader sequences are described.

If the metalloproteinase inhibitor does not assume its proper, active structure, any disulfide bonds which have formed and/or any noncovalent interactions which have occurred will first be disrupted by denaturing and reducing agents, for example, guanidinium chloride and 2-mercaptoethanol, before the metalloproteinase inhibitor is allowed to assume its active structure following dilution and oxidation of these agents under controlled conditions.

The transcription terminators contemplated herein serve to stabilize the vector. In particular, those sequences as described by Gentz et al., in Proc. Natl. Acad. Sci. USA 78: 4936–4940 (1981), specifically incorporated herein by reference, are contemplated for use in the present invention.

It is to be understood that application of the teachings of the present invention to a specific problem or environment will be within the capabilities of one having ordinary skill in the art in light of the teachings contained herein. Examples of the products of the present invention and representative processes for their isolation and manufacture appear in the following examples.

EXAMPLES

Example 1

Preparation of Poly(A$^+$) RNA from HEF-SA Fibroblasts

HEF-SA cells were grown to near confluence in 75 cm$^2$ T-flasks. Cells were washed twice in Dulbecco's phosphate buffered saline solution and harvested by the addition of 2 ml of 10 mM Tris, pH 7.5 containing 1% w/v SDS (obtained from BDH chemicals, Ltd., Poole, England), 5 mM EDTA and 20 ug/ml protease K (obtained from Boehringer Mannheim Biochemicals, Indianapolis, Ind.). Each flask was subsequently washed with an additional milliliter of this same solution.

The pooled aliquots from the cell harvest were made to 70 ug/ml in protease K and incubated at 40° C. for 45 minutes. The proteolyzed solution was brought to a NaCl concentration of 150 mM by the addition of 5 M stock and subsequently extracted with an equal volume of phenol:chloroform 1:1. The aqueous phase was reextracted with an equal volume of chloroform. Two volumes of ethanol were added to the aqueous phase and incubated overnight at –20° C. The precipitated nucleic acids were recovered by centrifugation at 17,500×g for 10 minutes in a Beckman J2–21 centrifuge, Beckman Instruments, Palo Alto, Calif., and were redissolved in 25 ml of 0.1% w/v SDS. This solution was again extracted with an equal volume of chloroform. The aqueous phase was added to two volumes of cold ethanol and kept at –20° C. for 2 hours. The precipitate was collected by centrifugation at 10,000×g for 15 minutes and redissolved in 10 ml of 1 mM Tris, 0.5 mM EDTA, 0.1% SDS, pH 7.5. RNA was precipitated from this solution by the addition of 10 ml of 4 M LiCl, 20 mM NaoAc, pH 5.0 and incubated at –20° C. for 18 hours. The precipitate was again recovered by centrifugation and washed twice with 2 M LiCl before redissolving in 1 mM Tris, 0.5 mM EDTA, 0.1% SDS, pH 7.5. This solution was stored at –70° C.

Chromatography on Oligo dT Cellulose

Total cellular RNA prepared as above was ethanol precipitated and redissolved in 0.5 M NaCl. Five ml of RNA at 0.45 mg/ml were applied to a 1 ml column of washed type VII oligo dT cellulose (obtained from PL Biochemicals, Milwaukee, Wis.). The column was then washed with 10 ml of 0.5 M NaCl and eluted with 2.0 ml of sterile H$_2$O. The eluted poly(A$^+$) fraction of RNA was ethanol precipitated and dissolved to give a 1 mg/ml solution in 1 mM Tris, 0.1 mM EDTA, pH 8.0. This was stored at –70° C.

cDNA Synthesis

Poly(A$^+$) RNA was primed with oligo dT (obtained from PL Biochemicals, Milwaukee, Wis.) to serve as a template for cDNA synthesis by AMV reverse transcriptase (obtained from Life Sciences, Inc., St. Petersburg, Fla.). Following the synthesis reaction, the RNA was hydrolyzed by the addition of 0.1 volume of 3 N NaOH and incubated at 67° C. for 10 minutes. The solution was then neutralized and the cDNA purified by gel filtration chromatography on biogel A 1.5 (obtained from BioRad Laboratories, Richmond, Calif.) in a 0.7×25 cm column in a 10 mM Tris, 5 mM EDTA, and 1% SDS, pH 7.5 solution. Fractions containing cDNA were pooled and concentrated by ethanol precipitation. The cDNA was dG tailed and purified by gel filtration using the procedure set forth above. Second strand synthesis was primed with oligo dC and polymerized in an initial reaction with the large (Klenow) fragment of DNA polymerase (obtained from Boehringer Mannheim). Following second strand synthesis, *E. coli* DNA polymerase I (obtained from Boehringer Mannheim) was added and incubation continued to form blunt ends. The double stranded cDNA was again purified by chromatography. EcoRI restriction sites within the cDNAs were modified by the action of EcoRI methylase, obtained from New England Biolabs, Beverly, Mass. The cDNA was again purified and ligated to synthetic EcoRI linkers. Finally, the ends were then trimmed with the endonuclease and the cDNA purified by gel filtration. This DNA was ligated into a unique EcoRI site in lambda gt10 DNA packaged in vitro and used to infect *E. coli* strain hflA according to the method set forth by Huynh, T. V., Young, R. A., and Davis, R. W., in *DNA Cloning Techniques*, A Practical Approach (ed. Glover, D. M.) (IRL Press Oxford), in press, specifically incorporated herein by reference. Approximately 25,000 recombinants were amplified in this manner.

Screening

Recombinant-phage-containing sequences of interest were selected by their preferential hybridization to synthetic oligonucleotides encoding portions of the primary structure of the desired metalloproteinase inhibitor, hereinafter referred to as FIBAC. These portions of the protein sequence correspond in part to those set forth in the published literature by Stricklin, G. P. and Welgus, H. G., J. Biol. Chem. 258: 12252–12258 (1983), specifically incorporated herein by reference. Recombinant phage were used to infect *E. coli* strain hflA and plated at a density of approximately 2×10³ pfu/150 mm petri dish. Phage were blotted onto nitrocellulose filters (BA85, Schleicher & Schuell Inc., Keene, N.H.), and DNA was denatured and fixed essentially as described by Benton and Davis in Science 196:180–182 (1979) specifically incorporated herein by reference.

Using that procedure, the filters were treated sequentially for 10–15 minutes each in 0.5 M NaCl, then 1.0 M Tris, 1.5 M NaCl pH 8.0, and finally submerged in 2× SSPE. (2× SSPE is 0.36 M NaCl, 20 mM NaH₂PO₄, 2 mM EDTA pH 7.4). Filters were blotted dry and baked 75°–80° for 3–4 hours. Duplicate filters were made of each plate. Filters were prehybridized for 1–3 hours at 37° in 5× SSPE containing 0.1× SET, 0.15% NaPPi, and 1× Denhardts solutions. Filters were then hybridized for 72 at 37° in this same solution containing 5×10⁵ cpm/ml of 5' end-labeled 51-mer oligonucleotide specific activity approximately 10⁶ cpm/pmole). Following hybridization, filters were washed six times in 5× SSPE containing 0.1× SET and 0.05% sodium pyrophosphate at 37°, then three times in 2× SSPE at 21°. These were then blotted dry and autoradiographed on Kodak XAR-5 film at −70° with a Kodak lightening-plus intensifying screen. Signals clearly visible from duplicate filters were used to pick phage for plaque purification. Filter preparations and hybridization procedures for plaque purification steps were the same as above. The washing procedure was simplified to 6 changes of 2× SSPE at 37°. Six isolates purified by repetitive plating were then arranged on a single lawn of E. coli strain C600 for testing with subsequent probes.

Preferential hybridization of the 17-mer to each of the isolates (as opposed to control plaques) was observed under a condition identical to that used for plaque purification. Probe C was used in a similar test, except that the SSPE concentration during hybridization was reduced to 4x. Again, each of the isolates demonstrated stronger hybridization to the probe than did control plaques.

Phage Purification and cDNA Characterization

Quantities of each of the six isolated phage were made by the plate stock technique and purified by serial CsCl block gradient centrifugation. DNA was extracted from these by dialysis against 50% formamide as described by Davis, R. W., Botstein, D., Roth, J. R., in *A Manual for Genetic Engineering: Advanced Bacterial Genetics*, 1980, Cold Spring Harbor Laboratory, specifically incorporated herein by reference. DNA from each of the isolates was digested with EcoRI and the products were analyzed by agarose gel electrophoresis. The insert from one of the larger clones, lambda FIBAC 5, was found to lack internal sites for SalI, HindIII, BamHI, and EcoRI. The cDNA insert was released from lambda FIBAC 5 DNA and the lambda arms digested by co-digesting with these four enzymes. The fragments were then ethanol-precipitated and ligated into the EcoRI site of plasmid pUC9 without further purification. These plasmids were then used to transform E. coli strain JM83. Transformants were selected on ampicillin containing plates. Plasmids from several transformants were purified and characterized on the basis of the EcoRI digestion products. One was selected which had an insert co-migrating with the insert from lambda FIBAC 5 on agarose gel electrophoresis. This plasmid has been named pUC9-F5/237P10.

Mapping and Subcloning

The insert in pUC9-F5/237P10 was mapped with respect to internal PstI sites. Double digests with EcoRI and PstI demonstrated three internal PstI recognition sites. The entire insert and the component pieces were subcloned into M13 bacteriophage mp19 and mp18, respectively. Sequencing of the pieces was performed by the dideoxynucleotide method described by Sanger et al. in Sanger, F., Nicklen, S., and Coulson, A. R., Proc. Natl. Acad. Sci. USA 74:5463–5467 (1977), specifically incorporated herein by reference.

The sequence of the DNA insert from pUC9-F5/237P10 showed an open reading frame which encodes the primary structure of a mature fibroblast collagenase inhibitor biologically equivalent to that isolable from human skin fibroblasts. The salient features of the sequence are:

(1) The insert is flanked by EcoRI restriction sites and by G/C and A/T homopolymeric tracts consistent with the cloning methodology;

(2) The coding strand is presented in the 5' to 3' convention with poly C at the 5' end and poly A at the 3' end, again consistent with the techniques employed;

(3) If the first G in the sequence GTTGTTG immediately adjacent to the 3' end of the poly C tract is considered as nucleotide 1, then an open reading frame is presented which encodes the primary structure of the mature human fibroblast collagenase inhibitor beginning at nucleotide 34 and continuing through nucleotide 585;

(4) The termination codon TGA at nucleotides 586 through 588 defines the carboxy terminus of the translation product which is the same as that of the mature protein;

(5) Nucleotides 1 through 33 define an amino acid sequence which is not found in the primary structure of the processed protein, but which is probably a portion of a leader peptide characteristic of secreted proteins;

(6) The three internal PstI sites have as their first base nucleotides 298, 327, and 448;

(7) There is a single recognition sequence for the restriction enzyme TthIIII beginning at nucleotide 78; and (8) There is a single recognition sequence for the restriction endonuclease NcoI beginning at nucleotide 227.

The sequence of nucleotides 1 through 703 and restriction site analysis are shown.

| | # SITES | FRAGMENTS | FRAG-MENTS | ENDS |
|---|---|---|---|---|
| ACC 1 (GTVWAC) | 1 214 | 495 (69.8) | 214 | 709 |
| | | 214 (30.2) | 1 | 214 |
| ALU 1 (AGCT) | 4 358 | 358 (50.5) | 1 | 358 |
| | 363 | 124 (17.5) | 482 | 606 |
| | 482 | 119 (16.8) | 363 | 482 |
| | 606 | 103 (14.5) | 606 | 709 |
| | | 5 ( 0.7) | 358 | 363 |
| AVA 1 (CQCGPG) | 1 | | | |
| | 536 | 536 (75.6) | 1 | 536 |
| | | 173 (24.4) | 536 | 709 |
| AVA 2 (GGRCC) | 3 | | | |
| | 257 | 257 (36.2) | 1 | 257 |
| | 477 | 220 (31.0) | 257 | 477 |
| | 572 | 137 (19.3) | 572 | 709 |
| | | 95 (13.4) | 477 | 572 |
| BBV 1 (GCTGC) | 1 | | | |
| | 269 | 440 (62.1) | 269 | 709 |
| | | 269 (37.9) | 1 | 269 |
| BST N1 (CCRGG) | 3 | | | |
| | 344 | 344 (48.5) | 1 | 344 |
| | 544 | 200 (28.2) | 344 | 544 |
| | 557 | 152 (21.4) | 557 | 709 |
| | | 13 ( 1.8) | 544 | 557 |
| DDE 1 (CTNAG) | 4 | | | |
| | 186 | 344 (48.5) | 365 | 709 |
| | 355 | 186 (26.2) | 1 | 186 |
| | 360 | 169 (23.8) | 186 | 355 |
| | 365 | 5 ( 0.7) | 360 | 365 |
| | | 5 ( 0.7) | 355 | 360 |
| ECO R1 (GAATTC) | 1 | | | |
| | 698 | 698 (98.4) | 1 | 698 |
| | | 11 ( 1.6) | 698 | 709 |

-continued

| # | SITES | FRAGMENTS | FRAG-MENTS | ENDS |
|---|---|---|---|---|
| FNU4H 1 (GCNGC) | 2 | | | |
| | 196 | 440 | (62.1) | 269 | 709 |
| | 269 | 196 | (27.6) | 1 | 196 |
| | | 73 | (10.3) | 196 | 269 |
| FOK 1 (GGATG) | 4 | | | |
| | 192 | 274 | (38.6) | 435 | 709 |
| | 204 | 192 | (27.1) | 1 | 192 |
| | 303 | 132 | (18.6) | 303 | 435 |
| | 435 | 99 | (14.0) | 204 | 303 |
| | | 12 | ( 1.7) | 192 | 204 |
| HAE 2 (PGCGCQ) | 1 | | | |
| | 368 | 368 | (51.9) | 1 | 368 |
| | | 341 | (48.1) | 368 | 709 |
| HAE 3 (GGCC) | 3 | | | |
| | 30 | 616 | (86.9) | 93 | 709 |
| | 63 | 33 | ( 4.7) | 30 | 63 |
| | 93 | 30 | ( 4.2) | 63 | 93 |
| | | 30 | ( 4.2) | 1 | 30 |
| HGI A1 (GRGCRC) | 1 | | | |
| | 552 | 552 | (77.9) | 1 | 552 |
| | | 157 | (22.1) | 552 | 709 |
| HHA 1 (GCGC) | 1 | | | |
| | 369 | 369 | (52.0) | 1 | 369 |
| | | 340 | (48.0) | 369 | 709 |
| HINC 2 (GTQPAC) | 1 | | | |
| | 118 | 591 | (83.4) | 118 | 709 |
| | | 118 | (16.6) | 1 | 118 |
| HINF 1 (GANTC) | 2 | | | |
| | 308 | 308 | (43.4) | 1 | 308 |
| | 587 | 279 | (39.4) | 308 | 587 |
| | | 122 | (17.2) | 587 | 709 |
| HPA 2 (CCGG) | 4 | | | |
| | 207 | 224 | (31.6) | 372 | 596 |
| | 372 | 207 | (29.2) | 1 | 207 |
| | 596 | 165 | (23.3) | 207 | 372 |
| | 654 | 58 | ( 8.2) | 596 | 654 |
| | | 55 | ( 7.8) | 654 | 709 |
| HPH 1 (GGTGA) | 2 | | | |
| | 380 | 380 | (53.6) | 1 | 380 |
| | 519 | 190 | (26.8) | 519 | 709 |
| | | 139 | (19.6) | 380 | 519 |
| MBO 2 (GAAGA) | 1 | | | |
| | 650 | 650 | (91.7) | 1 | 650 |
| | | 59 | ( 8.3) | 650 | 709 |
| MNL 1 (CCTC) | 5 | | | |
| | 81 | 193 | (27.2) | 81 | 274 |
| | 274 | 174 | (24.5) | 535 | 709 |
| | 406 | 132 | (18.6) | 274 | 406 |
| | 486 | 81 | (11.4) | 1 | 81 |
| | 535 | 80 | (11.3) | 406 | 486 |

-continued

| # | SITES | FRAGMENTS | FRAG-MENTS | ENDS |
|---|---|---|---|---|
| | | 49 | ( 6.9) | 486 | 535 |
| MST 2 (CCTNAGG) | 1 | | | |
| | 185 | 524 | (73.9) | 185 | 709 |
| | | 185 | (26.1) | 1 | 185 |
| NCI 1 (CCSGG) | 2 | | | |
| | 372 | 372 | (52.5) | 1 | 372 |
| | 595 | 223 | (31.5) | 372 | 595 |
| | | 114 | (16.1) | 595 | 709 |
| NCO 1 (CCATGG) | 1 | | | |
| | 227 | 482 | (68.0) | 227 | 709 |
| | | 227 | (32.0) | 1 | 227 |
| NSP B2 (CVGCWG) | 1 | | | |
| | 197 | 512 | (72.2) | 197 | 709 |
| | | 197 | (27.8) | 1 | 197 |
| PST 1 (CTGCAG) | 3 | | | |
| | 298 | 298 | (42.0) | 1 | 298 |
| | 327 | 261 | (36.8) | 448 | 709 |
| | 448 | 121 | (17.1) | 327 | 448 |
| | | 29 | ( 4.1) | 298 | 327 |
| SAU 1 (CCTNAGG) | 1 | | | |
| | 185 | 524 | (73.9) | 185 | 709 |
| | | 185 | (26.1) | 1 | 185 |
| SAU 3A (GATC) | 1 | | | |
| | 150 | 559 | (78.8) | 150 | 709 |
| | | 150 | (21.2) | 1 | 150 |
| SAU96 1 (GGNCC) | 5 | | | |
| | 29 | 220 | (31.0) | 257 | 477 |
| | 92 | 165 | (23.3) | 92 | 257 |
| | 257 | 137 | (19.3) | 572 | 709 |
| | 477 | 95 | (13.4) | 477 | 572 |
| | 572 | 63 | ( 8.9) | 29 | 92 |
| | | 29 | ( 4.1) | 1 | 29 |
| SCR F1 (CCNGG) | 5 | | | |
| | 344 | 344 | (48.5) | 1 | 344 |
| | 372 | 172 | (24.3) | 372 | 544 |
| | 544 | 114 | (16.1) | 595 | 709 |
| | 557 | 38 | ( 5.4) | 557 | 595 |
| | 595 | 28 | ( 3.9) | 344 | 372 |
| | | 13 | ( 1.8) | 544 | 557 |
| SFA N1 (GATGC) | 1 | | | |
| | 193 | 516 | (72.8) | 193 | 709 |
| | | 193 | (27.2) | 1 | 193 |
| TTH111 1 (GACNNNGTC) | 1 | | | |
| | 79 | 630 | (88.9) | 79 | 709 |
| | | 79 | (11.1) | 1 | 79 |

The following do not appear:

```
AAT 2     AFL 2     AFL 3     AHA 3
APA 1     ASU 2     AVA 3     AVR 2
BAL 1     BAM H1    BCL 1     BGL 1
BGL 2     BIN 1     BSSH 1    BST E2
CFR 1     CLA 1     ECO R5    FNUD 2
GDI 2     HAE 1     HGA 1     HGI C1
HGI D1    HGI J2    HIND 3    HPA 1
KPN 1     MLU 1     MST 1     NAE 1
NAR 1     NDE 1     NRU 1     NSP C1
PVU 1     PVU 1     RRU 1     RSA 1
SAC 1     SAC 2     SAL 1     SMA 1
SNA 1     SPH 1     STU 1     TAQ 1
XBA 1     XHO 1     XHO 2     XMA 3
XMN 1
```

```
          10         20         30         40         50         60
        GTTGTTGCTG TGGCTGATAG CCCCAGCAGG GCCTGCACCT GTGTCCCACC CCACCCACAG
                                         SH
                                         AA
                                         UE
                                         13
```

```
            70         80         90        100        110        120
     ACGGCCTTCT GCAATTCCGA CCTCGTCATC AGGGCCAAGT TCGTGGGGAC ACCAGAAGTC
          H          T  M           SH                            H
          A          T  N           AA                            I
          E          H  L           UE                            N
          3          1  1           13                            2

130        140        150        160        170        180
     AACCAGACCA CCTTATACCA GCGTTATGAG ATCAAGATGA CCAAGATGTA TAAAGGGTTC
                                   S
                                   A
                                   U
                                   A 190        200        210        220        230        240
     CAAGCCTTAG GGGATGCCGC TGACATCCGG TTCGTCTACA CCCCCGCCAT GGAGAGTGTC
           SD     FS FN      F  H       A           N
           AD     OF NS      O  P       C           C
           UE     KA UP      K  A       C           O
           11     11 12      1  2       1           1

250        260        270        280        290        300
     TGCGGATACT TCCACAGGTC CCACAACCGC AGCGAGGAGT TTCTCATTGC TGGAAAACTG
              A           B          M                             P
              V           B          N                             S
              A           V          L                             T
              2           1          1                             1

310        320        330        340        350        360
     CAGGATGGAC TCTTGCACAT CACTACCTGC AGTTTCGTGG CTCCCTGGAA CAGCCTGAGC
       F    H              P               B         D  A D
       O    I              S               S         D  L D
       K    N              T               T         E  U E
       1    1              1               1         1  1 1

370        380        390        400        410        420
     TTAGCTCAGC GCCGGGGCTT CACCAAGACC TACACTGTTG GCTGTGAGGA ATGCACAGTG
       A D  HH  N      H                            M
       L D  AH  C      P                            N
       U E  EA  I      H                            L
       1 1  21  1      1                            1

430        440        450        460        470        480
     TTTCCCTGTT TATCCATCCC CTGCAAACTG CAGAGTGGCA CTCATTGCTT GTGGACGGAC
                  F          P                                    A
                  O          S                                    V
                  K          T                                    A
                  1          1                                    2

490        500        510        520        530        540
     CAGCTCCTCC AAGGCTCTGA AAAGGGCTTC CAGTCCCGTC ACCTTGCCTG CCTGCCTCGG
       A   M                             H                     MA
       L   N                             P                     NV
       U   L                             H                     LA
       1   1                             1                     11

550        560        570        580        590        600
     GAGCCAGGGC TGTGCACCTG GCAGTCCCTG CGGTCCCAGA TAGCCTGAAT CCTGCCCGGA
       B          H   B               A            H          NH
       S          G   S               V            I          CP
       T          I   T               A            N          IA
       1          1   1               2            1          12

610        620        630        640        650        660
     GTGGAAGCTG AAGCCTGCAC AGTGTCCACC CTGTTCCCAC TCCCATCTTT CTTCCGGACA
       A                                              M      H
       L                                              B      P
       U                                              O      A
       1                                              2      2

670        680        690        700
     ATGAAATAAA GAGTTACCAC CCAGCAAAAA AAAAAAGGAA TTC
                                              E
                                              C
                                              O
                                              1
```

Example 2
Expression of Collagenase Inhibitor in E. coli

In this Example, a preferred method of coupling a preferred portable DNA sequence to the 5' end of the cloned cDNA is set forth. This involves making a nucleolytic cleavage at a specified point within the coding sequence and reconstructing the desired portion of the coding sequence by means of synthetic oligonucleotides in a manner that allows its excision and recombination (i.e., by incorporating useful restriction sites).

Trimming the 5' end of the coding region will be accomplished by synthesizing both strands of the DNA extending from the TthlllI site in the 5' direction and ending in a BamHI overhang. This synthetic oligonucleotide, referred to as FIBAC A, has the following features:

(1) Codon selection has been biased toward those most frequently found in the genes of highly expressed bacterial proteins;
(2) A methionine codon from which to initiate translation has been provided immediately upstream from the cysteine which begins the coding region of human processed FIBAC;
(3) The spacing of the BamHI site to the methionine codon is such that when cloned into pUC8, the coding region of FIBAC will be in-frame with the 5' end of the betagalactosidase gene;
(4) An in-frame stop codon and Shine Dalgarno sequence are also presented. Translation of this frame for the amino terminal portion of the beta-galactosidase is terminated at the TAA codon, and translation of FIBAC should be initiated at the following ATG;
(5) Codons have been selected to create a HqiAI site beginning with the G in the FIBAC initiation codon; and
(6) There is a PvuI site separated by one base from the 3' end of the BamHI sequence.

The structure of FIBAC A is

```
GA TCC GCG ATC GGA GTG TAA GAA ATG TGC ACT
   G CGC TAG CCT CAC ATT CTT TAC ACG TGA

TGC GTT CCG CCG CAT CCG CAG ACT GCT TTC
ACG CAA GGC GGC GTA GGC GTC TGA CGA AAG

TGC AAC TCT GAC C
ACG TTG AGA CTG GA
```

FIBAC A is synthesized using the ABI DNA synthesizer (Foster City, Calif.) as a series of four component oligonucleotides. Component oligonucleotide FA1 is:

GATCC GCGAT CGGAG TGTAA GAAAT GTGCA CTTGC

Component oligonucleotide FA2 is:

GGAACG CAAGT GCACA TTTCT TACAC TCCGA TCGCG

Component oligonucleotide FA3 is:

GTTC CGCCG CATCC GCAGA CTGCT TTCTG CAACT CTGAC C

Component oligonucleotide FA4 is:

AGGTC AGAGT TGCAG AAAGC AGTCT GCGGA TGCGG C

The remainder of the coding portion of the FIBAC gene is isolated as the 3' TthlllI to EcoRI fragment generated by a double digest of pUC9-F5/237P10 with these enzymes.

A synthetic linker is made to couple the 3' end of the TthlllI to EcoRI fragment to a SalI site. These oligonucleotides will be designed to recreate the SalI site and destroy the EcoRI site. The linker is comprised of the oligonucleotide linkers A1 and linker A2.

Linker A1 is: AATTGGCAG

Linker A2 is: TCGACTGCC

These oligonucleotides and oligonucleotides FA1–FA4 are kinased separately and annealed in equal molar ratios with the TthlllI to EcoRI 3' end of the cDNA and BamHI/SalI cut mpl9RF DNA. The ligated DNA is used to transfect JM105. Plaques are picked by their color in the presence of IPTG and X-gal and by hybridization to oligonucleotide FA2. Several positive plaques are to be sequenced. Those containing the designed sequence are subcloned into BamHI/SalI digested pUC8. Translation of the FIBAC gene in this construct is coupled to translation initiated for beta-galactosidase. This expression vector is referred to as pUC8-Fic.

Coupling translation of FIBAC to translation initiated for other highly expressed proteins is similarly arranged. For example, a portion of the OmpA gene which contains the Shine-Dalgarno and initiator methionine sequences has been synthesized. This sequence encodes the entire signal peptide of OmpA protein and had convenient restriction sites, including those for EcoRI, EcoRV, PvuI, and StuI.

The sequence of the sense strand is:

```
         10         20         30         40         50         60
GAATTCGATA TCTCGTTGGA GATATTCATG ACGTATTTTG GATGATAACG AGGCGCAAAA
E    T E                              F            M   H
C    A C                              O            N   H
O    Q O                              K            L   A
1    1 5                              1            1   1

70         80         90        100        110
AATGAAAAAG ACAGCTATCG CGATCGCAGT GGCACTGGCT GGTTTCGCTA CCGTA
           A    NF   PS
           L    RN   VA
           U    UU   UU
           1    12   1A
       120        130
GCGCA GGCCTCTGGT AAAAGCTT
H    S H M             H A
H    T A N             I L
A    U E L             N U
1    1 3 1             3 1
```

This sequence is hereinafter referred to as OmpA leader. Coupling the translation of FIBAC to OmpA is accomplished by cutting the pUC8-Fic with PvuI and SalI and isolating the coding region. This, together with the EcoRI to PvuI fragment isolated from OmpA leader, will be cloned into EcoRI/SalI-cut pUC8. As in the prior example, transcription is driven by the lac promoter and regulated by the lac I gene product at the lac operator. This FIBAC expression vector is referred to as pUC8-F/OmpAic.

To effect the translocation of FIBAC out of the inner cell membrane, an appropriate leader sequence is added to the amino terminus of FIBAC. The protein thus produced will be translocated and processed to yield the mature form.

To effect such a translocation, a FIBAC gene encoding the signal peptide of the E. coli OmpA protein continuous with the structural region of FIBAC is created. This particular FIBAC gene necessitates having in frame stop codons at the 5' end of the FIBAC coding region changed. To accomplish this, the portion of the 5' coding region from pUC8-Fic that extends from the HqiAI site to the NcoI site is isolated. Upstream sequences are resynthesized as a linker having cohesive ends from BamHI and HqiAI and containing an internal StuI site. This is synthesized as two oligonucleotides, linker B1 and linker B2.

Linker B1 is: GATCCCAGGCCTGCA

Linker B2 is: GGCCTGG

Linkers B1 and B2 are kinased separately and annealed in equal molar ratios with the HqiAI to NcoI fragment described above and BamHI/NcoI cut pUC8-Fic. The resulting construct has the coding sequence of FIBAC in frame with the translation of the amino terminus of beta-galactosidase. Translation of this sequence forms a fusion protein with FIBAC. This plasmid is referred to as pUC8-Ff.

Attaching the OmpA leader sequences to the coding region of FIBAC is accomplished by ligating EcoRI/StuI cut pUC8-Ff with an excess of the purified EcoRI to StuI fragment of OmpA leader. Following transformation, plasmids from several colonies will be characterized by hybridization. Those that have incorporated the OmpA leader fragment are characterized further to verify the structure. This plasmid, pUC8-F OmpAl, will direct the synthesis of a fusion protein beginning in the signal peptide of the E. coli OmpA protein and ending in human FIBAC. The signals present in the OmpA portion of the protein effect the protein's export from the cytoplasm and appropriate cleavage from the primary structure of FIBAC.

If the efficiency of expression were to be compromised by the sequence of the leader peptide or its combination with FIBAC either at the protein or at the nucleic acid level, the gene could be altered to encode any of several known E. coli leader sequences.

Transcription of all of the genes discussed is effected by the lac promoter. As in the case of initiation sites for translation, the promoter and operator region of the gene may be interchanged. FIBAC may also be expressed from vectors incorporating the lambda $P_L$ promoter and operator ($O_L$), and the hybrid promoter operator, Tac as described in Amann, E., Brosius, J., and Ptashne, M. Gene 25:167–178 (1983), specifically incorporated herein by reference. Excision of those portions of the gene including ribosome binding site structural region and 3' nontranslated sequences and insertion in alternate vectors containing the $P_L$ or Tac promoter makes use of the unique restriction sites that flank these structures in pUC8-F/OmpAic and pUC8-F/OmpAl. Insertion of the EcoRI to SalI fragment from either into similarly digested plasmid pDP8 effects transcription of these genes directed by the lambda $P_L$ promoter. Transcriptional regulation would be temperature sensitive by merit of the cI857 mutation harbored on this same plasmid.

Putting similar gene fragments into the transcription unit of the Tac promoter will be accomplished by first isolating the EcoRV to SalI fragment. This, together with the synthetic Tac promoter sequence which is flanked by BamHI and PvuII sites and which contains the lac operator will be inserted into the BamHI to SalI sites of pBR322 or preferably derivatives. The derivatives in this case refer to constructs containing either the lacI gene or the $I^q$ gene.

Expression of FIBAC in host microorganisms other than Escherichia is considered. Yeast and bacteria of the genera Bacillus, Pseudomonas, and Clostridium may each offer particular advantages. The processes outlined above could easily be adapted to others.

In general, expression vectors for any microorganism will embody features analogous to those which we have incorporated in the above mentioned vectors of E. coli. In some cases, it will be possible to simply move the specific gene constructs discussed above directly into a vector compatible with the new host. In others, it may be necessary or desirable to alter certain operational or structural elements of the gene.

Example 3

The human collagenase inhibitor may be readily purified after expression in a variety of microbes. In each case, the spectrum of contaminant proteins will differ. Thus, appropriate purification steps will be selected from a variety of steps already known to give a good separation of the human collagenase inhibitor from other proteins and from other procedures which are likely to work.

If the inhibitor is not secreted from the microbes, it may form inclusion bodies inside the recombinant microbes. These bodies are separated from other proteins by differential centrifugation after disruption of the cells with a French Press. The insoluble inclusion bodies are solubilized in 6 M guanidine hydrochloride or 8 M urea, and the inhibitor protein is more completely solubilized by reaction of its cysteines with sodium sulfite. At any time subsequent to this step, the cysteines are converted back to their reduced form with dithiothreitol. Once the inhibitor protein is solubilized from inclusion bodies, immunoaffinity chromatography using antibodies raised against the unfolded inhibitor are used for purification before refolding.

The inhibitor can be refolded according to the protocol mentioned in Example 6, infra. After refolding of the inhibitor, or if the inhibitor is secreted from the microbes, purification from other proteins is accomplished by a variety of methods. Initial steps include ultrafiltration through a 50 kD cutoff membrane or ammonium sulfate fractionation. Other useful methods include, but are not limited to, ion-exchange chromatography, gel filtration, heparin-sepharose chromatography, reversed-phase chromatography, or zinc-chelate chromatography. All of these steps have been successfully used in purification protocols. Additional high resolution steps include hydrophobic interaction chromatography or immunoaffinity chromatography. After purification, the metalloproteinase inhibitor is preferably at least 90–95% pure.

Example 4

Purification of Human Collagenase Inhibitor from Human Amniotic Fluid

Human amniotic fluid obtained from discarded amniocentesis samples was pooled and 6 liters were subjected to ultrafiltration through a 100 kD MW cutoff filter, obtained from Millipore Corporation, in a Millipore Pellicon Cassette System. The eluate was concentrated through a 10 kD cutoff filter, obtained from Millipore Corporation, then through an Amicon PM-10 membrane. Aliquots (10 ml) of concentrated amniotic fluid were eluted through a 2.5×100 cm column of Ultrogel AcA54, obtained from LKB Corporation, which was equilibrated with pH 7.6, 0.05 M hepes, 1 M sodium chloride, 0.01 M calcium chloride, and 0.02% sodium azide (all chemicals were obtained from sigma Chemical Company). Fractions containing the inhibitor were collected and pooled, dialyzed against pH 7.5, 0.025 M Hepes buffer containing 0.01 M calcium chloride and 0.02% sodium azide, and loaded onto a 1.5×28 cm heparin-sepharose CL-6B (obtained from Pharmacia, Inc.) column equilibrated with the same buffer. This column was rinsed with 1 liter of the above buffer and eluted with a linear gradient of 0–0.3 M sodium chloride. The fractions from the largest peak of inhibitor activity, eluting at about 0.1–0.15 M sodium chloride, were pooled, concentrated to 1 ml, and loaded onto a Synchropak rp-8 reverse phase HPLC column equilibrated with 0.05% trifluoroacetic acid (Aldrich Chemical Company). The column was eluted with a linear gradient of 0–40% acetonitrile (J. T. Baker Chemical Company) at ½% per minute. All fractions were immediately dried in a Savant speed-vac concentrator to remove acetonitrile, and redissolved in pH 7.5, 0.1 M Hepes before assay. The inhibitor eluted between 32–38% acetonitrile. Fractions containing the inhibitor were pooled, and 100 ul aliquots were eluted over a Bio-rad biosil-TSK 250 HPLC gel filtration column. The pooled peaks of inhibitor activity contained 0.1 mg of inhibitor, which was over 95% pure as judged by SDS-polyacrylamide gel electrophoresis.

Example 5
Purification of Human Fibroblast Collagenase Inhibitor from Human Embryonic Skin Fibroblast Serum-Free Medium Human embryonic skin fibroblasts were grown in serum-free tissue culture medium. Ten liters of this medium were collected, dialyzed against pH 7.5, 0.02 M hepes buffer containing 0.02% sodium azide and 0.01 M calcium chloride, and applied to a 2.8×48 cm column of heparin-sepharose CL-6B (Pharmacia, Inc.) equilibrated with the same buffer. The column was rinsed with 2 liters of this buffer and was then eluted with linear gradient of 0–0.3 M sodium chloride contained in this buffer. The fractions obtained were tested for the presence of inhibitor by their ability to inhibit human fibroblast collagenase. The fractions corresponding to the peak of activity were those obtained near 0.15 M sodium chloride. These fractions were concentrated to about 5 ml by ultrafiltration through an Amicon YM10 filter and the concentrate was applied in four separate runs to a 250×4.1 mm Synchropak rp-8 reverse phase HPLC column, equilibrated with 1% trifluoroacetic acid. The column was eluted with a 0–60% linear gradient of acetonitrile in 0.1% trifluoroacetic acid. The gradient was run at ½% acetontrile per minute. The inhibitor eluted in two sharp peaks between 26–29% acetonitrile. All fractions were immediately dried in a Savant speed-vac concentrator, redissolved in pH 7.5, 0.1 M Hepes, and assayed. At least 1.2 mg of collagenase inhibitor was recovered, which was 90–95% pure. This material gives a single band when run on a 17.5% reducing SDS gel. After carboxymethylation of t he cysteines and elution through the same rp-8 column under identical conditions, the inhibitor is suitably homogenous for protein sequencing.

Example 6

It is contemplated that the human collagenase inhibitor can be readily refolded into its native structure from its denatured state after expression of its gene in a microbe and separation of the collagenase inhibitor from most of the other proteins produced by the microbe. By analogy to the conditions necessary for the refolding of other disulfide-contanning proteins as set forth by Freedman, R. B. and Hillson, D. A., in "Formation of Disulfide Bonds," In: *The Enzymology of Post-Translational Modification of Proteins*, Vol. 1, R. B. Freedman and H. C. Hawkins, eds., pp. 158–207 (1980), specifically incorporated herein by reference, refolding of the human collagenase inhibitor should occur in solutions with a pH of 8.0 or greater. At this pH, the cysteines of the protein are partially ionized, and this condition is necessary for the attainment of native disulfide bond pairings. The inhibitor concentration should be relatively low, less than 0.1 mg/ml, to minimize the formation of intermolecular disulfide-linked aggregates which will interfere with the refolding process.

Since the stability of the refolded (native) disulfide bonded structure relative to the unfolded (reduced) structure depends on both the solution oxidation-reduction potential and the concentrations of other redox-active molecules, it is contemplated that the redox potential should be buffered with a redox buffer giving a potential equivalent to a reduced: oxidized glutathione ratio of 10. The preferred concentration range of reduced glutathione would be 0.1–1.0 mM. At higher concentrations, mixed disulfides will form with protein, reducing the yield of the refolded (native) structure. The relative stabilities of the unfolded protein and the native structure, and thus the rate and yield of refolding, will also depend on other solution variables, such as the pH, temperature, type of hydrogen-ion buffer, ionic strength, and the presence or absence of particular anions or cations as discussed in Privalov, P. L., "Stability of Proteins, Small Globular Proteins," in *Advances in Protein Chemistry*, Vol. 33, pp. 167–236, (1979), specifically incorporated herein by reference. These conditions vary for every protein and can be determined experimentally. It is contemplated that addition of any molecule that strongly prefers to bind the native (as opposed to the unfolded) structure, and which can be readily separated afterwards from the native (refolded) protein, will increase not only the yield but the rate of re-folding. These molecules include monoclonal antibodies raised against the native structure, and other proteins which tightly bind the native collagenase such as the mammalian enzymes collagenase or gelatinase.

Example 7

The second preferred sequence as set forth herein, i.e.,

```
           10         20         30         40         50         60
GGCCATCGCC GCAGATCCAG CGCCCAGAGA GACACCAGAG AACCCACCAT GGCCCCCTTT
H          F          XB         HH                    N          S
A          N          HI         AH                    C          A
E          U          ON         EA                    0          U
3          1          21         21                    1          1
```

-continued

```
         70         80         90        100        110        120
GACCCCTGGC TTCTGCATCC TGTTGTTGCT GTGGCTGATA GCCCCAGCAG GGCCTGCACC
     B          S F                                   S          H
     S          F O                                   A          A
     T          A K                                   U          E
     1          1 1                                   1          3

130        140        150        160        170        180
TGTGTCCCAC CCCACCCACA GACGGCCTTC TGCAATTCCG ACCTCGTCAT CAGGGCCAAG
                H                    T          M              S H
                A                    T          N              A A
                E                    H          L              U E
                3                    1          1              1 3

190        200        210        220        230        240
TTCGTGGGGA CACCAGAAGT CAACCAGACC ACCTTATACC AGCGTTATGA GATCAAGATG
                H                                          S
                I                                          A
                N                                          U
                2                                          A 250        260        270        280        290        300
ACCAAGATGT ATAAAGGGTT CCAAGCCTTA GGGGATGCCG CTGACATCCG GTTCGTCTAC
                          S D        F S   F N     F   H       A
                          A D        O F   N S     0   P       C
                          U E        K A   U P     K   A       C
                          1 1        1 1   1 2     1   2       1

310        320        330        340        350        360
ACCCCCGCCA TGGAGAGTGT CTGCGGATAC TTCCACAGGT CCCACAACCG CAGCGAGGAG
     N                                 A          B         M
     C                                 V          B         N
     0                                 A          V         L
     1                                 2          1         1

370        380        390        400        410        420
TTTCTCATTG CTGGAAAACT GCAGGATGGA CTCTTGCACA TCACTACCTG CAGTTTCGTG
                P          F   H                        P
                S          0   I                        S
                T          K   N                        T
                1          1   1                        1

430
GCTCCCTGGA AC
     B
     S
     T
     1
``` has the following restriction sites:

| # | SITES | FRAGMENTS | FRAG-MENTS | ENDS |
|---|---|---|---|---|
| ACC 1 (GTVWAC) | | | | |
| 1 | | | | |
| | 295 | 295 | (68.3) | 1 | 295 |
| | | 137 | (31.7) | 295 | 432 |
| AVA 2 (GGRCC) | | | | |
| 1 | | | | |
| | 338 | 338 | (78.2) | 1 | 338 |
| | | 94 | (21.8) | 338 | 432 |
| BBV 1 (GCTGC) | | | | |
| 1 | | | | |
| | 350 | 350 | (81.0) | 1 | 350 |
| | | 82 | (19.0) | 350 | 432 |
| BIN 1 (GGATC) | | | | |
| 1 | | | | |
| | 14 | 418 | (96.8) | 14 | 432 |
| | | 14 | ( 3.2) | 1 | 14 |
| BST N1 (CCRGG) | | | | |
| 2 | | | | |
| | 65 | 360 | (83.3) | 65 | 425 |
| | 425 | 65 | (15.0) | 1 | 65 |
| | | 7 | ( 1.6) | 425 | 432 |

| # | SITES | FRAGMENTS | FRAG-MENTS | ENDS |
|---|---|---|---|---|
| DDE 1 (CTNAG) | | | | |
| 1 | | | | |
| | 267 | 267 | (61.8) | 1 | 267 |
| | | 165 | (38.2) | 267 | 432 |
| FNU4H 1 (GCNGC) | | | | |
| 3 | | | | |
| | 8 | 269 | (62.3) | 8 | 277 |
| | 277 | 82 | (19.0) | 350 | 432 |
| | 350 | 73 | (16.9) | 277 | 350 |
| | | 8 | ( 1.9) | 1 | 8 |
| FOK 1 (GGATG) | | | | |
| 4 | | | | |
| | 76 | 197 | (45.6) | 76 | 273 |
| | 273 | 99 | (22.9) | 285 | 384 |
| | 285 | 76 | (17.6) | 1 | 76 |
| | 384 | 48 | (11.1) | 384 | 432 |
| | | 12 | ( 2.8) | 273 | 285 |
| HAE 2 (PGCGCQ) | | | | |
| 1 | | | | |
| | 19 | 413 | (95.6) | 19 | 432 |
| | | 19 | ( 4.4) | 1 | 19 |
| HAE 3 (GGCC) | | | | |
| 5 | | | | |
| | 1 | 258 | (59.7) | 174 | 432 |

-continued

| # | SITES | FRAGMENTS | FRAG-MENTS | ENDS |
|---|---|---|---|---|
| | 51 | 60 (13.9) | 51 | 111 |
| | 111 | 50 (11.6) | 1 | 51 |
| | 144 | 33 ( 7.6) | 111 | 144 |
| | 174 | 30 ( 6.9) | 144 | 174 |
| | | 1 ( 0.2) | 1 | 1 |
| HHA 1 (GCGC) | | | | |
| 1 | | | | |
| | 20 | 412 (95.4) | 20 | 432 |
| | | 20 ( 4.6) | 1 | 20 |
| HINC 2 (GTQPAC) | | | | |
| 1 | | | | |
| | 199 | 233 (53.9) | 199 | 432 |
| | | 199 (46.1) | 1 | 199 |
| HINF 1 (GANTC) | | | | |
| 1 | | | | |
| | 389 | 389 (90.0) | 1 | 389 |
| | | 43 (10.0) | 389 | 432 |
| HPA 2 (CCGG) | | | | |
| 1 | | | | |
| | 288 | 288 (66.7) | 1 | 288 |
| | | 144 (33.3) | 288 | 432 |
| MNL 1 (CCTC) | | | | |
| 2 | | | | |
| | 162 | 193 (44.7) | 162 | 355 |
| | 355 | 162 (37.5) | 1 | 162 |
| | | 77 (17.8) | 355 | 432 |
| MST 2 (CCTNAGG) | | | | |
| 1 | | | | |
| | 266 | 266 (61.6) | 1 | 266 |
| | | 166 (38.4) | 266 | 432 |
| NCO 1 (CCATGG) | | | | |
| 2 | | | | |
| | 47 | 261 (60.4) | 47 | 308 |
| | 308 | 124 (28.7) | 308 | 432 |
| | | 47 (10.9) | 1 | 47 |
| NSP B2 (CVGCWG) | | | | |
| 1 | | | | |
| | 278 | 278 (64.4) | 1 | 278 |
| | | 154 (35.6) | 278 | 432 |
| PST 1 (CTGCAG) | | | | |
| 2 | | | | |
| | 379 | 379 (87.7) | 1 | 379 |
| | 408 | 29 ( 6.7) | 379 | 408 |
| | | 24 ( 5.6) | 408 | 432 |
| SAU 1 (CCTNAGG) | | | | |
| 1 | | | | |
| | 266 | 266 (61.6) | 1 | 266 |
| | | 166 (38.4) | 266 | 432 |
| SAU 3A (GATC) | | | | |
| 2 | | | | |
| | 14 | 217 (50.2) | 14 | 231 |
| | 231 | 201 (46.5) | 231 | 432 |
| | | 14 ( 3.2) | 1 | 14 |
| SAU96 1 (GGNCC) | | | | |
| 4 | | | | |
| | 51 | 165 (38.2) | 173 | 338 |
| | 110 | 94 (21.8) | 338 | 432 |
| | 173 | 63 (14.6) | 110 | 173 |
| | 338 | 59 (13.7) | 51 | 110 |
| | | 51 (11.8) | 1 | 51 |
| SCR F1 (CCNGG) | | | | |
| 2 | | | | |
| | 65 | 360 (83.3) | 65 | 425 |
| | 425 | 65 (15.0) | 1 | 65 |
| | | 7 ( 1.6) | 425 | 432 |
| SFA N1 (GATGC) | | | | |
| 2 | | | | |
| | 75 | 199 (46.1) | 75 | 274 |
| | 274 | 158 (36.6) | 274 | 432 |
| | | 75 (17.4) | 1 | 75 |
| STY 1 (CCRRGG) | | | | |
| 2 | | | | |
| | 47 | 261 (60.4) | 47 | 308 |
| | 308 | 124 (28.7) | 308 | 432 |
| | | 47 (10.9) | 1 | 47 |

-continued

| | # | SITES | FRAGMENTS | FRAG-MENTS | ENDS |
|---|---|---|---|---|---|
| TTH111 1 (GACNNNGTC) | | | | | |
| | 1 | | | | |
| | | 160 | 272 (63.0) | 160 | 432 |
| | | | 160 (37.0) | 1 | 160 |
| XHO 2 (PGATCQ) | | | | | |
| | 1 | | | | |
| | | 13 | 419 (97.0) | 13 | 432 |
| | | | 13 ( 3.0) | 1 | 13 |

The following do not appear:

| | | | |
|---|---|---|---|
| AAT 2 | AFL 2 | AFL 3 | AHA 2 |
| AHA 3 | ALU 1 | APA 1 | ASU 2 |
| AVA 1 | AVA 3 | AVR 2 | BAL 1 |
| BAM H1 | BAN 1 | BAN 2 | BCL 1 |
| BGL 1 | BGL 2 | BSM 1 | BSP 1286 |
| nSSH 1 | BST E2 | CFR 1 | CLA 1 |
| ECO R1 | ECO R5 | FNUD 2 | GDI 2 |
| HAE 1 | HGA 1 | HGI A1 | HGI C1 |
| HGI D1 | HGI J2 | HIND 3 | HPA 1 |
| HPH 1 | KPN 1 | MBO 2 | MLU 1 |
| MST 1 | NAE 1 | NAR 1 | NCI 1 |
| NDE 1 | NHE 1 | NOT 1 | NRU 1 |
| NSP C1 | PVU 1 | PVU 2 | RRU 1 |
| RSA 1 | SAC 1 | SAC 2 | SAL 1 |
| SCA 1 | SMA 1 | SNA 1 | SNA B1 |
| SPE 1 | SPH 1 | SSP 1 | STU 1 |
| TAQ 1 | XBA 1 | XHO 1 | XMA 3 |
| XMN 1 | | | |

The salient features of this cDNA are:

1. The coding strand is presented in the 5' to 3' convention with the polyC tract at the 5' end.

2. If the first G in the sequence GGC CAT CGC CGC is considered as nucleotide 1, then an open reading frame exists from nucleotide 1 through nucleotide 432, which is the 3' end of this partial cDNA.

3. The first methionine in this reading frame is encoded by nucleotides 49 through 51 and represents the initiation site of translation.

4. The amino acid sequence prescribed by nucleotides 49 through 114 is not found in the primary structure of the mature protein, but it is the sequence of the leader peptide of human protein.

5. The sequence of nucleotides 82 through 432 is identical to the sequence of nucleotides numbered 1 through 351 in the insert from the first preferred sequence of Example 1.

6. The amino acid sequence of the mature protein displays two consensus sequences for sugar attachment. These sequences, -N-Q-T- prescribed by nucleotides 202 through 210 and -N-R-S- prescribed by nucleotides 346 through 354, are amino acid residues 30 through 32 and 78 through 80, respectively, in the mature protein. Both sites are glycosylated in the human inhibitor protein.

It will be apparent to those skilled in the art that various modifications and variations can be made in the processes and products of the present invention. Thus, it is intended that the present invention cover the modifications and variations of this invention provided they come within the scope of the appended claims and their equivalence.

What is claimed is:

1. A purified DNA sequence encoding a human collagenase inhibitor, said sequence comprising:

```
         10          20          30          40
GTTGTTGCTG  TGGCTGATAG  CCCCAGCAGG  GCCTGCACCT 50          60          70          80
GTGTCCCACC  CCACCCACAG  ACGGCCTTCT  GCAATTCCGA 90         100         110         120
CCTCGTCATC  AGGGCCAAGT  TCGTGGGGAC  ACCAGAAGTC 130         140         150         160
AACCAGACCA  CCTTATACCA  GCGTTATGAG  ATCAAGATGA 170         180         190         200
CCAAGATGTA  TAAAGGGTTC  CAAGCCTTAG  GGGATGCCGC 210         220         230         240
TGACATCCGG  TTCGTCTACA  CCCCCGCCAT  GGAGAGTGTC 250         260         270         280
TGCGGATACT  TCCACAGGTC  CCACAACCGC  AGCGAGGAGT
```

-continued
```
        370         380         390         400
TTAGCTCAGC  GCCGGGGCTT  CACCAAGACC  TACACTGTTG 410         420         430         440
GCTGTGAGGA  ATGCACAGTG  TTTCCCTGTT  TATCCATCCC 450         460         470         480
CTGCAAACTG  CAGAGTGGCA  CTCATTGCTT  GTGGACGGAC 490         500         510         520
CAGCTCCTCC  AAGGCTCTGA  AAAGGGCTTC  CAGTCCCGTC 530         540         550         560
ACCTTGCCTG  CCTGCCTCGG  GAGCCAGGGC  TGTGCACCTG 570         580         590         600
GCACTCCCTG  CGGTCCCAGA  TAGCCTGAAT  CCTGCCCGGA 610         620         630         640
GTGGAAGCTG  AAGCCTGCAC  AGTGTCCACC  CTGTTCCCAC 650         660         670         680
TCCCATCTTT  CTTCCGGACA  ATGAAATAAA  GAGTTACCAC 690         770
CCAGCAAAAA  AAAAAAGGAA  TTC.
```

2. A purified DNA sequence encoding a human collagenase inhibitor, said sequence comprising:

```
         10         20         30         40         50         60
GGCCATCGCC GCAGATCCAG CGCCCAGAGA GACACCAGAG AACCCACCAT GGCCCCCTTT 70         80         90        100        110        120
GACCCCTGGC TTCTGCATCC TGTTGTTGCT GTGGCTGATA GCCCCAGCAG GGCCTGCACC 130        140        150        160        170        180
TGTGTCCCAC CCCACCCACA GACGGCCTTC TGCAATTCCG ACCTCGTCAT CAGGGCCAAG 190        200        210        220        230        240
TTCGTGGGGA CACCAGAAGT CAACCAGACC ACCTTATACC AGCGTTATGA GATCAAGATG 250        260        270        280        290        300
ACCAAGATGT ATAAAGGGTT CCAAGCCTTA GGGGATGCCG CTGACATCCG GTTCGTCTAC 310        320        330        340        350        360
ACCCCCGCCA TGGAGAGTGT CTGCGGATAC TTCCACAGGT CCCACAACCG CAGCGAGGAG 370        380        390        400        410        420
TTTCTCATTG CTGGAAAACT GCAGGATGGA CTCTTGCACA TCACTACCTG CAGTTTCGTG 430        440        450        460        470        480
GCTCCCTGGA ACAGCCTGAG CTTAGCTCAG CGCCGGGGCT TCACCAAGAC CTACACTGTT 490        500        510        520        530        540
GGCTGTGAGG AATGCACAGT GTTTCCCTGT TTATCCATCC CCTGCAAACT GCAGAGTGGC 550        560        570        580        590        600
ACTCATTGCT TGTGGACGGA CCAGCTCCTC AAGGCTCTG AAAAGGGCTT CCAGTCCCGT 610        620        630        640        650        660
CACCTTGCCT GCCTGCCTCG GGAGCCAGGG CTGTGCACCT GGCAGTCCCT GCGGTCCCAG 670        680        690        700        710        720
ATAGCCTGAA TCCTGCCCGG AGTGGAAGCT GAAGCCTGCA CAGTGTCCAC CCTGTTCCCA 730        740        750        760        770        780
CTCCCATCTT TCTTCCGGAC AATGAAATAA AGAGTTACCA CCCAGCAAAA AAAAAAGGA.
```

-continued
```
        290        300        310        320
TTCTCATTGC TGGAAAACTG CAGGATGGAC TCTTGCACAT 330        340        350        360
CACTACCTGC AGTTTGCTGG CTCCCTGGAA CAGCCTGAGC
```

3. A recombinant-DNA cloning vector comprising a nucleotide sequence encoding a human collagenase inhibitor, said nucleotide sequence comprising:

```
         10         20         30         40         50         60
GTTGTTGCTG TGGCTGATAG CCCCAGCAGG GCCTGCACCT GTGTCCCACC CCACCCACAG 70         80         90        100        110        120
ACGGCCTTCT GCAATTCCGA CCTCGTCATC AGGGCCAAGT TCGTGGGGAC ACCAGAAGTC 130        140        150        160        170        180
AACCAGACCA CCTTATACCA GCGTTATGAG ATCAAGATGA CCAAGATGTA TAAAGGGTTC 190        200        210        220        230        240
CAAGCCTTAG GGGATGCCGC TGACATCCGG TTCGTCTACA CCCCCGCCAT GGAGAGTGTC 250        260        270        280        290        300
TGCGGATACT TCCACAGGTC CCACAACCGC AGCGAGGAGT TTCTCATTGC TGGAAAACTG 310        320        330        340        350        360
CAGGATGGAC TCTTGCACAT CACTACCTGC AGTTTCGTGG CTCCCTGGAA CAGCCTGAGC 370        380        390        400        410        420
TTAGCTCAGC GCCGGGCTT CACCAAGACC TACACTGTTG GCTGTGAGGA ATGCACAGTG 430        440        450        460        470        480
TTTCCCTGTT TATCCATCCC CTGCAAACTG CAGAGTGGCA CTCATTGCTT GTGGACGGAC 490        500        510        520        530        540
CAGCTCCTCC AAGGCTCTGA AAAGGGCTTC CAGTCCCGTC ACCTTGCCTG CCTGCCTCGG 550        560        570        580        590        600
GAGCCAGGGC TGTGCACCTG GCAGTCCCTG CGGTCCCAGA TAGCCTGAAT CCTGCCCGGA 610        620        630        640        650        660
GTGGAAGCTG AAGCCTGCAC AGTGTCCACC CTGTTCCCAC TCCCATCTTT CTTCCGGACA 670        680        690        700
ATGAAATAAA GAGTTACCAC CCAGCAAAAA AAAAAAGGAA TTC.
```

4. A recombinant-DNA cloning vector comprising a nucleotide sequence encoding a human collagenase inhibitor, said nucleotide sequence comprising:

```
                      10         20         30         40         50         60
             GGCCATCGCC GCAGATCCAG CGCCCAGAGA GACACCAGAG AACCCACCAT GGCCCCCTTT 70         80         90        100        110        120
             GACCCCTGGC TTCTGCATCC TGTTGTTGCT GTGGCTGATA GCCCCAGCAG GGCCTGCACC 130        140        150        160        170        180
             TGTGTCCCAC CCCACCCACA GACGGCCTTC TGCAATTCCG ACCTCGTCAT CAGGGCCAAG 190        200        210        220        230        240
             TTCGTGGGGA CACCAGAAGT CAACCAGACC ACCTTATACC AGCGTTATGA GATCAAGATG 250        260        270        280        290        300
             ACCAAGATGT ATAAAGGGTT CCAAGCCTTA GGGGATGCCG CTGACATCCG GTTCGTCTAC 310        320        330        340        350        360
             ACCCCCGCCA TGGAGAGTGT CTGCGGATAC TTCCACAGGT CCCACAACCG CAGCGAGGAG 370        380        390        400        410        420
             TTTCTCATTG CTGGAAAACT GCAGGATGGA CTCTTGCACA TCACTACCTG CAGTTTCGTG 430        440        450        460        470        480
             GCTCCCTGGA ACAGCCTGAG CTTAGCTCAG CGCCGGGCT TCACCAAGAC CTACACTGTT 490        500        510        520        530        540
             GGCTGTGAGG AATGCACAGT GTTTCCCTGT TTATCCATCC CCTGCAAACT GCAGAGTGGC 550        560        570        580        590        600
             ACTCATTGCT TGTGGACGGA CCAGCTCCTC CAAGGCTCTG AAAAGGGCTT CCAGTCCCGT 610        620        630        640        650        660
             CACCTTGCCT GCCTGCCTCG GGAGCCAGGG CTGTGCACCT GGCAGTCCCT GCGGTCCCAG 670        680        690        700        710        720
             ATAGCCTGAA TCCTGCCCGG AGTGGAAGCT GAAGCCTGCA CAGTGTCCAC CCTGTTCCCA 730        740        750        760        770        780
             CTCCCATCTT TCTTCCGGAC AATGAAATAA AGAGTTACCA CCCAGCAAAA AAAAAAGGA.
```

5. The vector pUC9-F5/237P10.

6. A recombinant-DNA method for microbial production of a human collagenase inhibitor comprising:
   (a) culturing a host microorganism under conditions wherein said inhibitor is expressed, said microorganism containing the vector of claim 3, said vector comprising a nucleotide sequence encoding a human collagenase inhibitor; and
   (b) harvesting said inhibitor.

7. A recombinant-DNA method for microbial production of a human collagenase inhibitor comprising:
   (a) culturing a host microorganism under conditions wherein said inhibitor is expressed, said microorganism containing the vector of claim 4, said vector comprising a nucleotide sequence encoding a human collagenase inhibitor; and
   (b) harvesting said inhibitor.

8. The microorganism C600/pUC9-F5/237P10 having A.T.C.C. accession number 53003.

* * * * *

UNITED STATES PATENT AND TRADEMARK OFFICE
CERTIFICATE OF CORRECTION

PATENT NO.    : 6,090,585
DATED         : July 18, 2000
INVENTOR(S)   : David F. Carmichael et al.

It is certified that error appears in the above-identified patent and that said Letters Patent is hereby corrected as shown below:

Column 39, claim 1,
Line 65, "AGTTTGCTGG" should read -- AGTTTCGTGG --.

Column 40, claim 1,
Line 16, "GCACTCCCTG" should read -- GCAGTCCCTG --.

Signed and Sealed this

Thirtieth Day of March, 2004

JON W. DUDAS
*Acting Director of the United States Patent and Trademark Office*